United States Patent
Ahearn et al.

(10) Patent No.: US 9,408,995 B2
(45) Date of Patent: **\*Aug. 9, 2016**

(54) NITROUS OXIDE ANESTHETIC ADMINISTRATION SYSTEM

(71) Applicant: David J Ahearn, Little Compton, RI (US)

(72) Inventors: David J. Ahearn, Little Compton, RI (US); Edward Carey, Westport, MA (US)

(73) Assignee: David J. Ahearn, Little Copmton, RI (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/317,853

(22) Filed: Jun. 27, 2014

(65) Prior Publication Data

US 2015/0075525 A1 Mar. 19, 2015

Related U.S. Application Data

(63) Continuation-in-part of application No. 13/681,509, filed on Nov. 20, 2012, now Pat. No. 8,794,233, which is a continuation of application No. 12/890,176, filed on Sep. 24, 2010, now Pat. No. 8,371,297, which is a continuation-in-part of application No. 12/567,729, filed on Sep. 25, 2009, now Pat. No. 8,360,058.

(60) Provisional application No. 61/840,419, filed on Jun. 27, 2013, provisional application No. 61/100,149, filed on Sep. 25, 2008.

(51) Int. Cl.
*A61M 11/00* (2006.01)
*A61M 16/12* (2006.01)
*A61M 16/00* (2006.01)
(Continued)

(52) U.S. Cl.
CPC ......... *A61M 16/122* (2014.02); *A61M 16/0078* (2013.01); *A61M 16/01* (2013.01); *A61M 16/104* (2013.01); *A61M 16/202* (2014.02); *A61M 16/009* (2013.01); *A61M 2016/003* (2013.01); *A61M 2202/0208* (2013.01); *A61M 2202/0283* (2013.01); *A61M 2205/18* (2013.01); *A61M 2205/3331* (2013.01);
(Continued)

(58) Field of Classification Search
USPC .......................... 128/203.28, 204.18, 204.23
See application file for complete search history.

(56) References Cited

U.S. PATENT DOCUMENTS 340,778 A    4/1886  Gilbert
2,225,201 A  12/1940 Anderson
(Continued)

FOREIGN PATENT DOCUMENTS

EP           0584439 A1   2/1994

*Primary Examiner* — Steven Douglas
(74) *Attorney, Agent, or Firm* — Adler Pollock & Sheehan P.C.; Daniel J. Holmander, Esq.; George N. Chaclas, Esq.

(57) ABSTRACT

A system and method for administering nitrous oxide to a patient has a fluid control system that allows a user to monitor and control the supply of gases to a patient. A shutoff valve allows a user to selectively activate the fluid control system. Oxygen flow is adjusted by a flow controlling valve. A differential pressure regulator allows flow of nitrous oxide in response to sufficient oxygen flow. Flow of the nitrous oxide is further controlled by a ratio controlling valve. A display shows the flow of the gases through the fluid control system. A flush valve allows a user to flush the output with oxygen. A flow indicator light may be included. An optional output selector allows the user to direct the flow to one of various output ports. An optional safety scavenge valve prevents operation of the fluid control system when there is insufficient scavenge vacuum pressure.

16 Claims, 32 Drawing Sheets

(51) Int. Cl.
  *A61M 16/10* (2006.01)
  *A61M 16/01* (2006.01)
  *A61M 16/20* (2006.01)

(52) U.S. Cl.
  CPC ... *A61M 2205/3334* (2013.01); *A61M 2205/50* (2013.01); *A61M 2209/082* (2013.01); *Y02C 20/10* (2013.01)

(56) References Cited

U.S. PATENT DOCUMENTS

| | | | |
|---|---|---|---|
| 3,176,687 A | 4/1965 | Barach | |
| 3,198,574 A | 8/1965 | Ota et al. | |
| 3,259,430 A | 7/1966 | Beach | |
| 3,262,735 A | 7/1966 | Thompson | |
| 3,761,968 A | 10/1973 | Besler | |
| 3,785,377 A | 1/1974 | Jorgensen | |
| 3,802,736 A | 4/1974 | Valeska et al. | |
| 4,109,958 A | 8/1978 | Grupelli | |
| 4,114,946 A | 9/1978 | Hoffmeister et al. | |
| 4,188,946 A | 2/1980 | Watson et al. | |
| 4,310,307 A | 1/1982 | Bellisario | |
| 4,391,588 A | 7/1983 | Matsui | |
| 4,538,605 A | 9/1985 | Gedeon et al. | |
| 4,934,933 A | 6/1990 | Fuchs | |
| 5,411,019 A | 5/1995 | Smith | |
| 5,676,133 A | 10/1997 | Hickle et al. | |
| 6,234,172 B1 | 5/2001 | Ausbourne et al. | |
| 6,412,801 B1 | 7/2002 | Izuchukwu et al. | |
| 6,626,496 B2 | 9/2003 | Beach et al. | |
| 6,948,493 B2 | 9/2005 | Dunlop | |
| 8,794,233 B2 | 8/2014 | Ahearn et al. | |
| 2003/0145854 A1 | 8/2003 | Hickle | |
| 2008/0122269 A1 | 5/2008 | Tatlock | | and emergency air intake assembly 6; an intermediate N2O connection 7; a scavenge vacuum tube 8; a N2O tube 9; a N2O tube connector 10; N2O and scavenging tubing connectors 11; a scavenge vacuum tube connector 12; a breather bag 13; and a scavenging vacuum tube holder 16.

NITROUS OXIDE ANESTHETIC ADMINISTRATION SYSTEM

CROSS REFERENCE TO RELATED APPLICATIONS

This application is related to and claims priority from earlier filed U.S. provisional patent application Ser. No. 61/840,419 filed Jun. 27, 2013, and is a continuation-in-part of U.S. patent application Ser. No. 13/681,509 filed Nov. 20, 2012, which was a continuation of U.S. patent application Ser. No. 12/890,176 filed Sep. 24, 2010 now U.S. Pat. No. 8,371,297 issued Feb. 12, 2013, which was a continuation-in-part of U.S. patent application Ser. No. 12/567,729 filed Sep. 25, 2009 now U.S. Pat. No. 8,360,058 issued Jan. 29, 2013, which was a U.S. non-provisional patent application of U.S. provisional patent application Ser. No. 61/100,149 filed Sep. 25, 2008, the entire contents of each of which are incorporated herein by reference.

BACKGROUND OF THE INVENTION

The present invention relates to a system for administering gas. More particularly, the present invention relates to a system for administering anesthesia/analgesia gas which provides convenient, direct access by a medical practitioner, a clear line of vision for the medical practitioner, and flexibility to accommodate the patient and medical professional's needs. The present invention also relates to a fluid control system for such a gas administering system and a method of operating the fluid control system.

N2O analgesia has been used for over a century to successfully relax and sedate dental patients. Originally and until recently the application of these gages was virtually unrestricted and thus the supply system required was relatively unencumbered. With the advent of mandatory scavenge systems for nitrous delivery, these units became much more bulky and difficult to use in day to day practice and this utilized rate declined.

Typically, the compressed medical gages are delivered to the practitioner's facility in gas cylinders. These cylinders either connect to a central distribution system, serving multiple operating rooms, or they are portable and are mounted on rolling carts which serve one operating room and patient. These cylinders are connected via hoses or piping to a regulating system which controls delivery pressure, flow rate and blended ratio. There are monitors, gages and other devices to provide information to the practitioner regarding the delivery parameters. From the control device, gas flows via flexible hoses to a nasal delivery interface device. As shown in FIG. 1, vacuum scavenging of expelled gases flows from the nasal delivery interface device, via flexible tubing, into the centralized building vacuum utility system.

These essential components are incorporated into support systems. Systems commonly found in the art fall into three general categories: a) cart mounted tanks and controls, b) cart mounted controls and c) wall or stationary cabinet mounted controls.

Cart mounted tanks and control systems utilize an open or closed, wheeled cart. (FIGS. 4, 9). Portable O2 and N2O tanks are mounted on the cart. The control system and breather bag are usually mounted on a center pole attached to an open cart or supported by the shell of an enclosed cart. The patient supply tubing connects the cart outlet to the nasal delivery interface device. Referring to FIG. 2, the scavenging tubing connects the nasal delivery interface device via flexible tubing into the centralized building vacuum utility system.

As illustrated in FIGS. 1-2, current systems running from the control devices to the nasal delivery interface device use multi lumen hose systems which are long, heavy, complex and somewhat stiff. They pull on the patient's head and limit practitioner accessibility to the patient's mouth area. As a result they also limit the ability of the practitioner to reposition the patient's head.

FIG. 1 shows a generic nitrous oxide anaesthetic administration system having a N2O and scavenging nasal shell 3, 4; a N2O and scavenging tubing 5; a breather bag connection Cart mounted control systems are similar to those above, except that the O2 and N2O are supplied from a central source via floor or wall gas outlets rather than from in situ tanks. Flexible hoses route the gases from the outlet to the control system. The control system and breather bag are mounted on a center pole attached to an open, wheeled cart. The patient supply tubing connects the cart outlet to the nasal delivery interface device. The scavenging tubing connects the nasal delivery interface device via flexible tubing into the centralized building vacuum utility system.

As illustrated in FIG. 3, wall and cabinet mounted systems have the O2 and N2O gas supplied via flexible or rigid tubing from a central source. This tubing is enclosed in the walls of the operatory with other centralized utilities. The control system and breather bag are mounted to the wall or cabinet unit. The mounting may be a flush mount, surface or articulated arm mount design. Long patient supply tubing connects the control systems to the nasal delivery interface device on the patient. Long scavenging system tubing connects the nasal delivery interface device into the centralized building vacuum utility system.

Also, wall mounted systems are typically separated from the patient chair by a work surface or passageway. Wall mount systems have long hose lengths between the control devices and the nasal delivery interface device. The longer the hose length, the longer the latency period between changing a control setting and the patient actually receiving that changed gaseous output. In addition, the hose position and length interferes with operator positioning. Tubing runs from the wall mounted, control system outlet to the nasal delivery interface device. This tubing crosses a passageway or work surface and blocks or encumbers which ever of these it traverses.

As illustrated in FIGS. 4-8, cart mounted systems can be located behind one of the practitioners or tucked under the back of the patient chair. In either case, visual monitoring of critical information in impeded. This is a dangerous situation because unknown changes occurring in the gaseous anesthetic system can be detrimental to the patient. Additionally, excess gas expelled into the operatory is harmful to the practitioners.

Also, carts located in the passageways, or workplace around the patient chair, cause inference as the practitioners move around the patient. Staff can trip over the carts and be injured and the flow of other technology and emergency access is impeded. As well as the cost of damaging an anesthetic system, rupturing any high pressure, 2000 psi, system can be very dangerous to all occupants of the operatory.

There are two main drawbacks of the systems describe above. First, current systems usually put the system controls out of direct reach of the medical professional when he/she is seated in normal treatment positions. This limitation is especially burdensome with wall mounted systems. This makes it difficult for the medical professional to accomplish anesthetic system adjustments without walking around or reaching around the patient. This awkward arrangement slows access and response to emergency situations. Second, current systems often put monitoring device displays and gauges out of direct view of the doctor and assistant.

Therefore, it would be particularly desirable to provide a system or method for anesthesia/analgesia gas delivery provides a nitrous oxide anesthetic administration system which provides convenient, direct access by a medical practitioner, a clear line of vision for the medical practitioner, and flexible to accommodate the patient and professional's needs. Currently, there is no known nitrous oxide anesthetic administration system in the prior art which provides these benefits.

BRIEF SUMMARY OF THE INVENTION

An embodiment of the present invention preserves the advantages of prior art nitrous oxide anesthetic administration systems or methods. In addition, it provides new advantages not found in currently available nitrous oxide anesthetic administration systems or methods and overcomes many disadvantages of such currently available nitrous oxide anesthetic administration systems or methods.

The present invention is a system for administering nitrous oxide which is preferably attached to a patient chair. The system generally includes: a mounting surface structure, a fluid control system attached to the mounting surface structure, a nasal delivery interface system connected to a patient and fluid control system, a nitrous oxide and oxygen supply connected to the fluid control system, a vacuum source for scavenging, a breather bag connected to the fluid control system, a mounting plate assembly to interface with patient or dental chairs, an adjustable post mechanism attached to the mounting plate assembly and the mounting surface structure, supply gas connectors and mixed gas output connectors attached to the fluid control system, and other hardware and tubing that is necessary to administer nitrous oxide in a health care environment, preferably a dentist's office.

The system includes an adjustable post mechanism attached to a patient or dental chair. The adjustable post mechanism is attached to a mounting plate assembly which is attached to a lower portion of a patient chair. The adjustable post mechanism is configured for height adjustment and pivotal adjustment to provide convenience of use to a practitioner.

The mounting surface structure includes a top surface and a bottom surface. The bottom surface of the mounting surface structure is attached to a top end of the adjustable post mechanism. The mounting surface structure positioned along a horizontal axis or approximately 180 degrees. The mounting surface structure attached to a breather bag a proximal end and a fluid control system at a distal end closest to a practitioner.

A fluid control system for controlling the flow of nitrous oxide and oxygen is attached to the mounting surface structure. The fluid control system including a fluid flow meter mounted on a top surface of the fluid control system. A display of the fluid flow meter positioned along a vertical axis at less than 90 degrees relative to the mounting surface structure to provide a better view to the practitioner. A nitrous oxide and oxygen supply fluidly connected to the fluid control system using fluid connectors fixedly attached to the bottom surface of said mounting surface structure.

A nasal delivery interface system fluidly connected to the fluid control system. The nasal delivery interface system including a single scavenging tube and a single nitrous oxide and oxygen tube fluidly connected to a single nasal delivery mask. The fluid control system including a mixed gas output connector fluidly connected to the single nitrous oxide and oxygen tube. A vacuum source fluidly connected to the single scavenging tube for scavenging excess gases and the fluid control system.

A breather bag is vertically mounted to a top surface of the mounting surface structure. The breather bag positioned along a vertical axis or about 90 degrees depending upwardly from the mounting surface structure. The breather bag mounted rearward or behind of the fluid control system to allow full view of fluid flow meter display. The breather bag fluidly connected to the control system by way of an elongated tubular structure attached to a front surface of the fluid flow meter.

The fluid control system also includes a safety scavenge system including a mass airflow sensor, master controller, nitrous oxide valve, and alarm. The mass airflow sensor reads the scavenging vacuum pressure which it communicates to the master controller. Depending upon the scavenging vacuum pressure, the master controller can activate an alarm or shut off the flow of nitrous oxide. In operation, the present invention provides a system for administering anesthesia/analgesia gas which prevents excessively high volumes of exhaled nitrous oxide in the operatory environment through monitoring of the scavenge vacuum pressure.

The safety scavenge system more specifically includes the following components. The mass airflow sensor for reading scavenging vacuum pressure is fluidly connected to the scavenging tube before the vacuum source. The master controller in electrical communication with the mass airflow sensor for receiving the scavenging vacuum pressure reading from the mass airflow sensor which is compared to a predetermined range. A visual alarm is in electrical communication with the master controller which instructs the visual alarm to activate if the scavenging vacuum pressure is less than a first predetermined range. An audio alarm is in electrical communication with the master controller which instructs the audio alarm to activate of the scavenging vacuum pressure is less than a second predetermined range. A nitrous oxide valve is fluidly connected to the nitrous oxide supply and in electrical communication with the master controller which shuts off the nitrous oxide shut-off valve when the scavenging vacuum pressure is less than a third predetermined range.

In operation, the present invention provides a system for administering anesthesia/analgesia gas which provides convenient and direct access to a medical practitioner. The practitioner connects the nasal delivery interface system to the patient and to the fluid control system. After the nasal mask is attached to the patient, the nitrous oxide/oxygen gas is turned on and the gas enters a single tube fluidly connected with a nasal delivery mask. Throughout the administration of the gas, the system allows the practitioner a direct view and a close proximity to the upright breathing bag, fluid control system including display, patient, and all other parts of the nitrous oxide administration system which makes the administration of the gas much more efficient, safe, and less time consuming. Also, the mounting of the nitrous oxide anesthetic administration system to a patient's chair provides greater stability and convenience to a practitioner.

When the vacuum source is operational, any excess gases are scavenged from the patient through the nasal delivery mask, along a single scavenging tube, and returns back through the fluid control system. By only having two tubes, the patient and practitioner are given additional space and movement and reduce the possibility of entanglement.

In addition, the present invention includes the following method for administering nitrous oxide to a patient. First, a fluid generated by a vacuum source is provided. Second, nitrous oxide fluid from a nitrous oxide source is provided. Third, a means for scavenging excess nitrous oxide is in fluid connection with the nitrous oxide source and the vacuum source. Fourth, a safety scavenge system is connected to the fluid connection between the nitrous oxide source and the vacuum source. The safety scavenge system includes a mass airflow sensor, master controller, alarm, and nitrous oxide valve. Fifth, the means for scavenging excess nitrous oxide is connected to the vacuum source and the nitrous oxide source onto a patient. Sixth, a flow rate flow rate of the vacuum source is increased to provide fluid into the safety scavenge system. Seventh, nitrous oxide is released through the safety scavenge system upon the vacuum source reaching a predetermined range. Eighth, excess nitrous oxide is retrieved from the means for scavenging excess nitrous oxide using the vacuum source. Ninth, the vacuum source is decreased below the third predetermined range which prevents the safety control valve from releasing nitrous oxide. The safety scavenge system actuated by flow fluids to control the release of nitrous oxide therethrough.

The present invention also provides a fluid control system that allows a user to selectively allow flow of gas through the gas administering system, and to control the ratio of gases flowing through the gas administering system.

The exemplary embodiment of the fluid control system has a first intake conduit for receiving a first gas from a first gas source, such as an oxygen tank, and has a second intake conduit for receiving a second gas from a second gas source, such as a nitrous oxide tank. A shutoff valve on the first intake conduit allows a user to selectively allow the first gas to flow through the first conduit. A flow controlling valve is located at the joint of the first intake conduit and the first output conduit, and allows a user to adjust the flow of the first gas into the first output conduit.

The exemplary embodiment of the fluid control system does not allow the second gas to flow into the system if the flow of the first gas is below a threshold level. For this purpose, the flow meter includes a differential pressure regulator having a first chamber and a second chamber that are separated by a movable, spring biased wall. When the first gas flows from the first intake conduit and provides sufficient pressure on the wall, it opposes the spring bias on the wall between the first and second chambers. The movable wall is moved to allow the second intake conduit and second chamber to be fluidly connected to a second output conduit.

A user can adjust the flow of the second gas after it has passed through the differential pressure regulator by way of a ratio controlling valve on the second output conduit.

Thus, during operation of the fluid control system, a user can independently adjust the flow the first gas and the second gas through the first output conduit and the second output conduit, respectively. A display unit shows the flow of the first gas through the first output conduit, and the flow of the second gas through the second output conduit.

The flow of the first and second gases is combined in a combined flow conduit, which is fluidly connected to the first output conduit and the second output conduit.

The fluid control system preferably includes a flush valve that allows a user to selectively open a direct connection between the first intake conduit and the combined output conduit.

The fluid control system also preferably includes a flow indicator light that indicates whether a first gas is flowing through the first intake conduit.

The flow control system also preferably includes an output selector valve that allows a user to selectively connect the combined output conduit to one of a plurality of output ports.

The fluid control system also preferably includes a safety scavenge valve along the second intake conduit, which is movable between a spring biased closed position and an open position. The safety scavenge valve is connected to the vacuum of the scavenge system. When the scavenge system is deactivated or providing insufficient vacuum pressure, the safety scavenge valve is spring biased to a closed position, and the second gas cannot flow through the second intake conduit towards the combined output conduit. Sufficient vacuum pressure in the scavenge system opposes the spring bias of the safety scavenge valve and opens it to allow the second gas to flow through the second intake conduit.

This fluid control system can be provided independently to a user, or a manufacturer can incorporate it into a nitrous oxide anesthetic administration system such as the one disclosed herein.

It is therefore an object of the present invention to provide a method or system for a nitrous oxide anesthetic administration system which provides convenient access to nitrous oxide for a practitioner and patient.

It is a further object of the present invention to have direct access to the fluid control system and patient during administration of the nitrous oxide.

It is also an object of the present invention to provide a clear line of vision for the medical practitioner and flexibility to accommodate the patient and practitioner's needs.

Another object of the present invention is to eliminate the problems associated with current nitrous oxide delivery and scavenging systems.

Furthermore, another object of the present is to provide greater safety to patients and medical or dental persons during release of nitrous oxide in a medical or dental office.

A further object of the present invention is to provide a system for administering anesthesia/analgesia gas which prevents excessively high volumes of exhaled nitrous oxide in the operatory environment through monitoring of the scavenge vacuum pressure A further object of the present invention is to provide a flow meter that allows a user to control flow of two fluids in a system for administering anesthesia/analgesia gas. The flow meter allows a user to independently adjust flow of two fluid through the system. The flow meter displays the flow of each of the fluids in being combined in the system. The flow meter optionally includes an output selector for connecting the system to multiple outputs. The flow meter optionally includes a safety scavenge valve.

Other objects, features and advantages of the invention shall become apparent as the description thereof proceeds when considered in connection with the accompanying illustrative drawings.

BRIEF DESCRIPTION OF THE DRAWINGS

The novel features which are characteristic of the nitrous oxide anesthetic administration systems and methods are set forth in the appended claims. However, the nitrous oxide anesthetic administration systems and methods, together with further embodiments and attendant advantages, will be best understood by reference to the following detailed description taken in connection with the accompanying drawings in which:

DETAILED DESCRIPTION OF PREFERRED EMBODIMENTS

Figure 1:
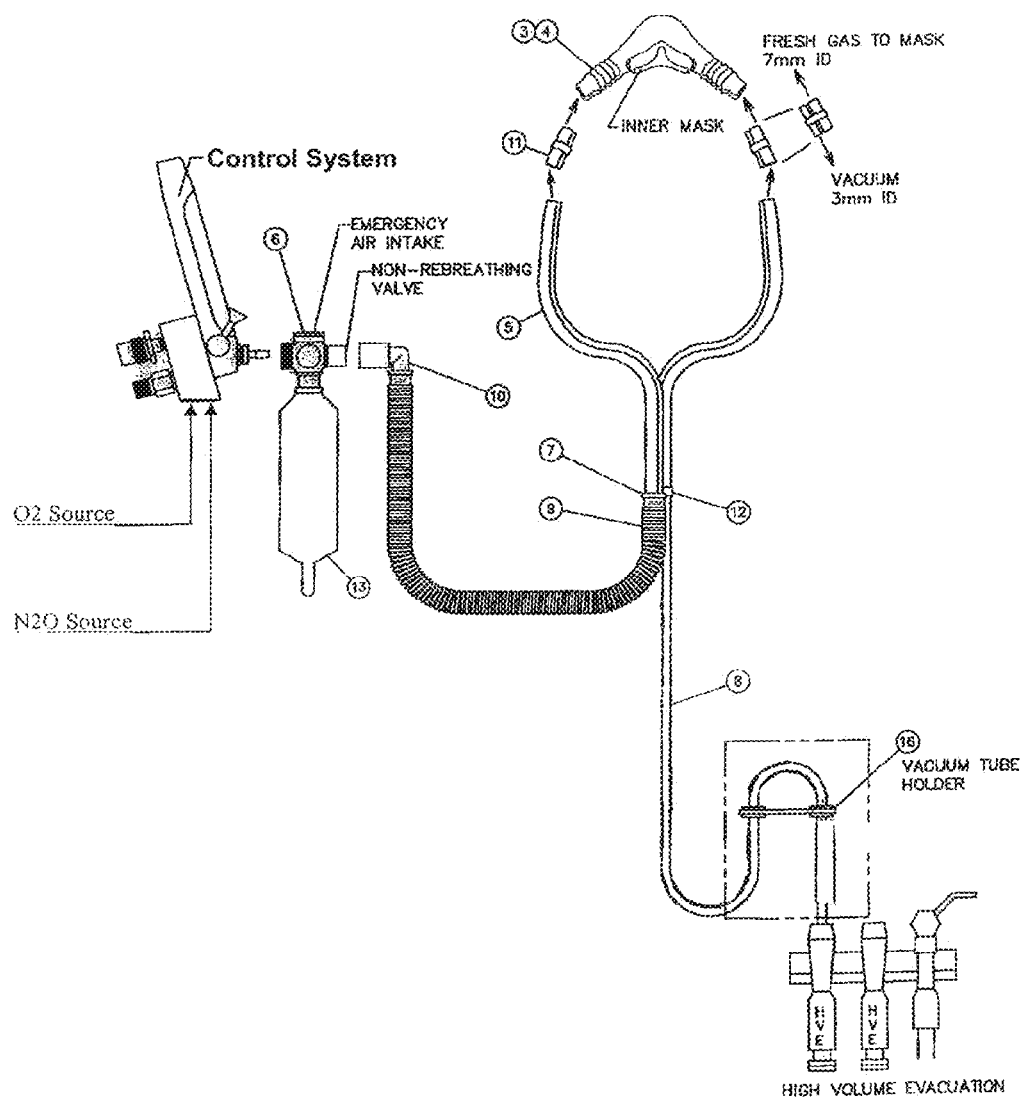
FIG. 1 is a prior art nitrous oxide anesthetic administration system.
Figure 2:
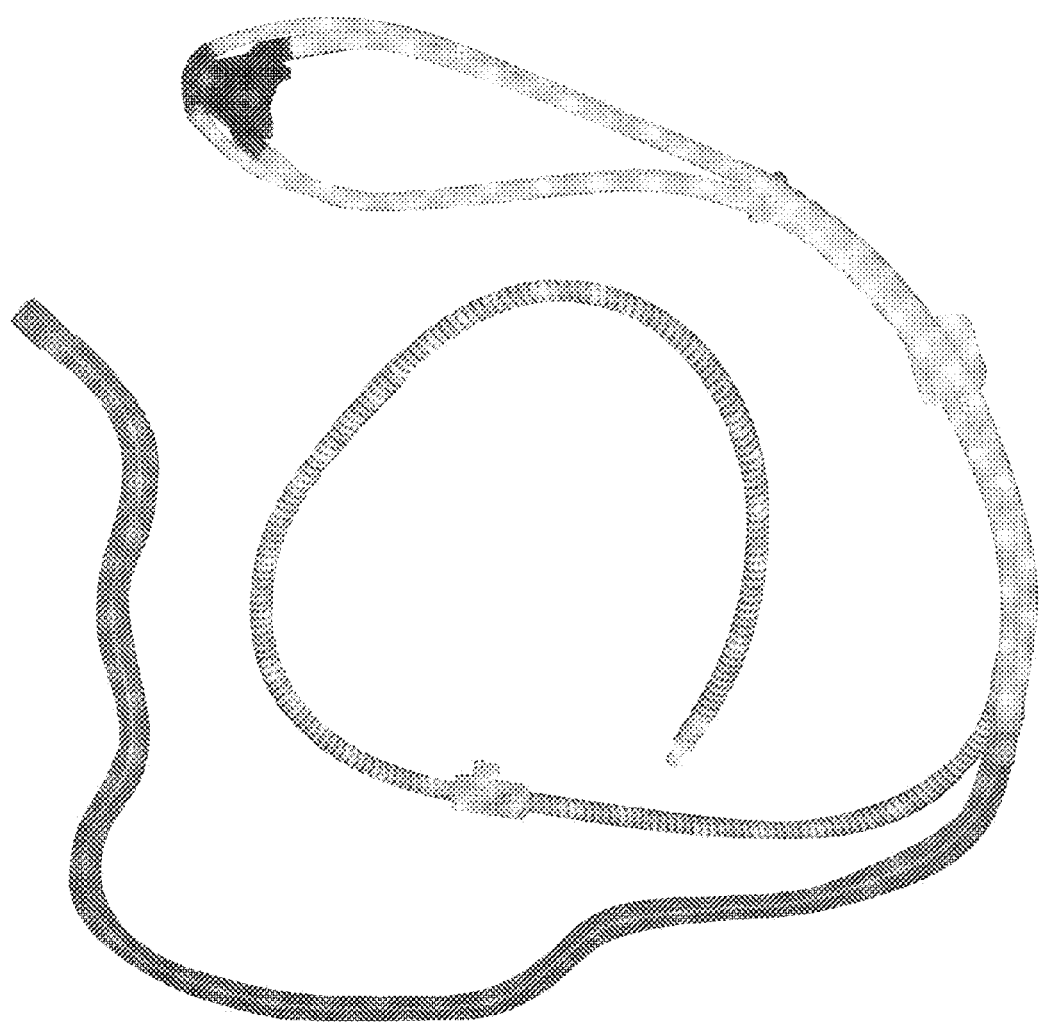
FIG. 2 is prior art nasal delivery interface device.
Figure 3:
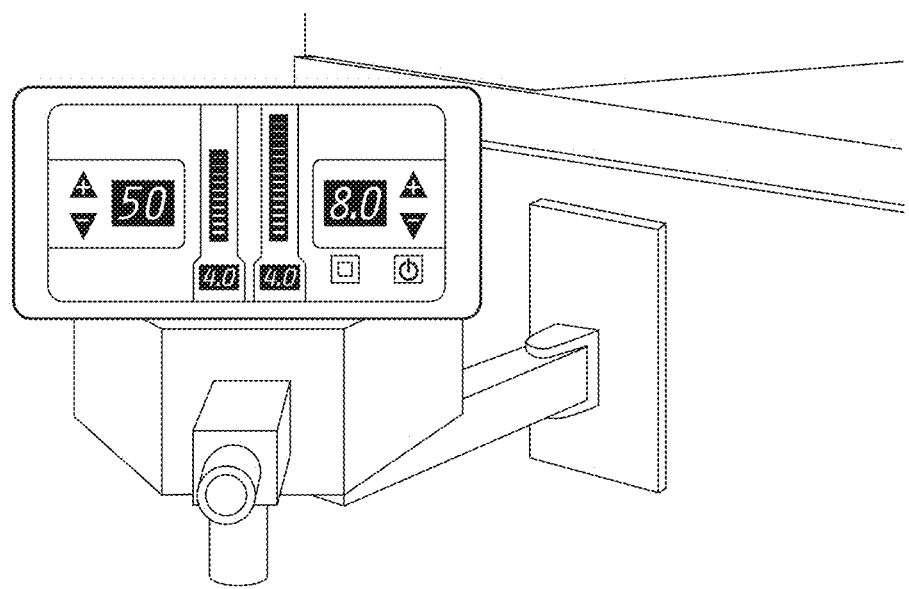
FIG. 3 is a prior art wall mounted nitrous oxide anesthetic administration system.
Figure 4:
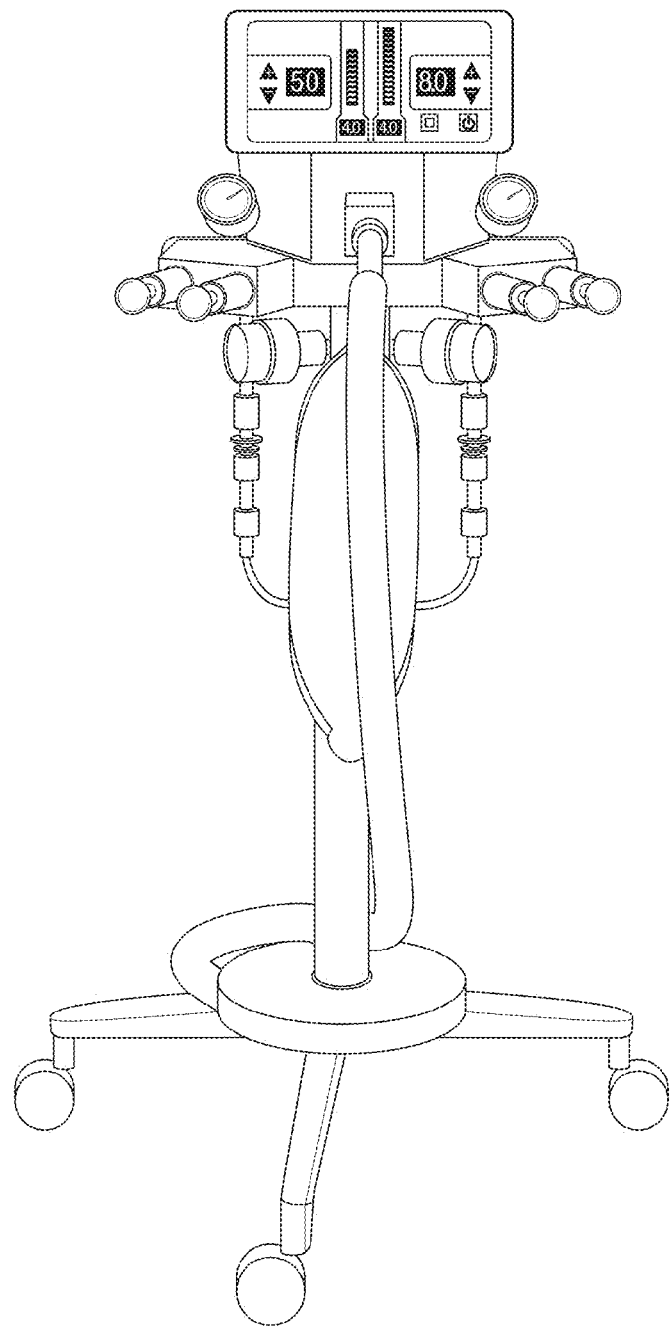
FIG. 4 is a prior art cart mounted nitrous oxide anesthetic administration system.
Figure 5:
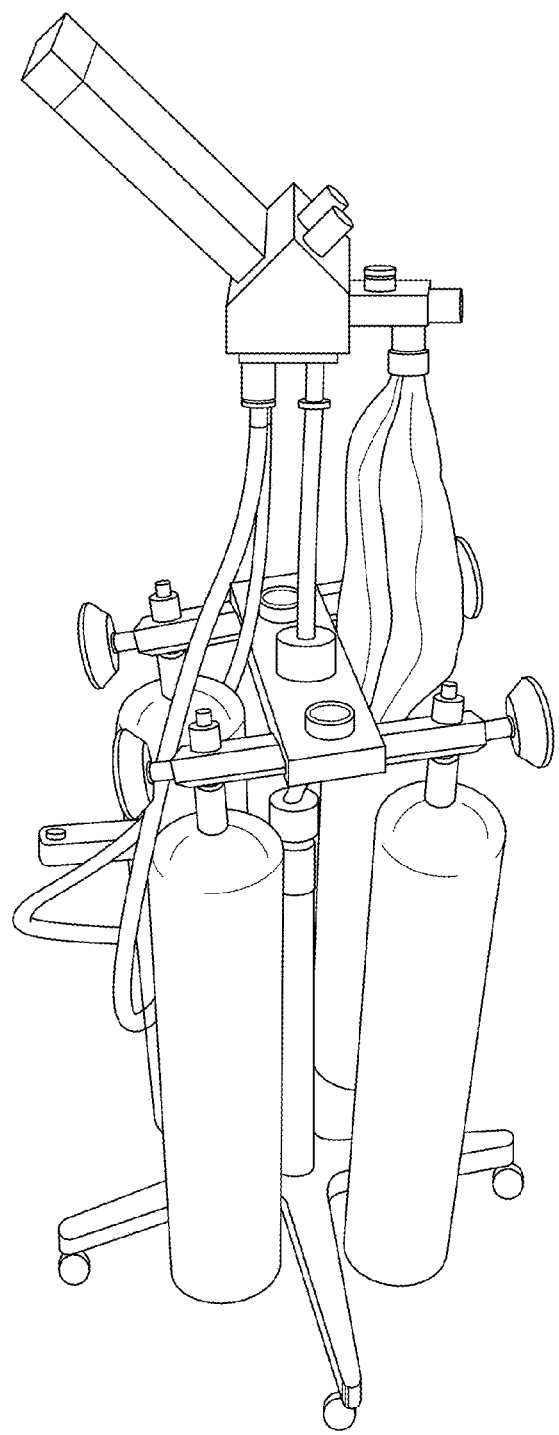
FIG. 5 is a prior art cart mounted nitrous oxide anesthetic administration system.
Figure 6:
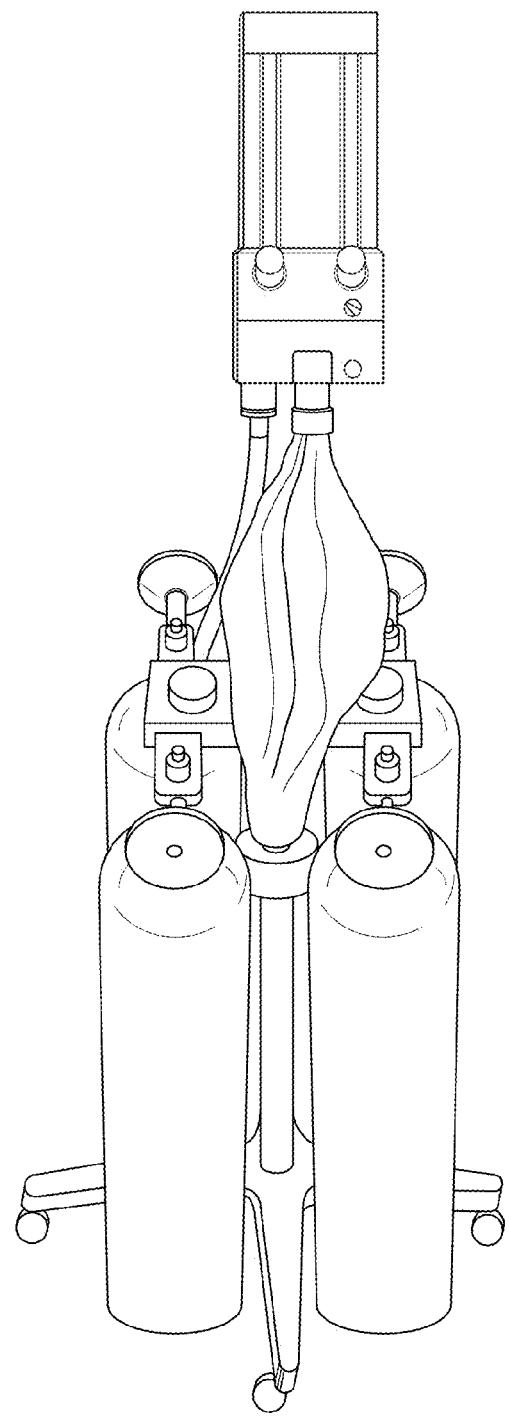
FIG. 6 is a prior art cart mounted nitrous oxide anesthetic administration system of FIG. 5.
Figure 7:
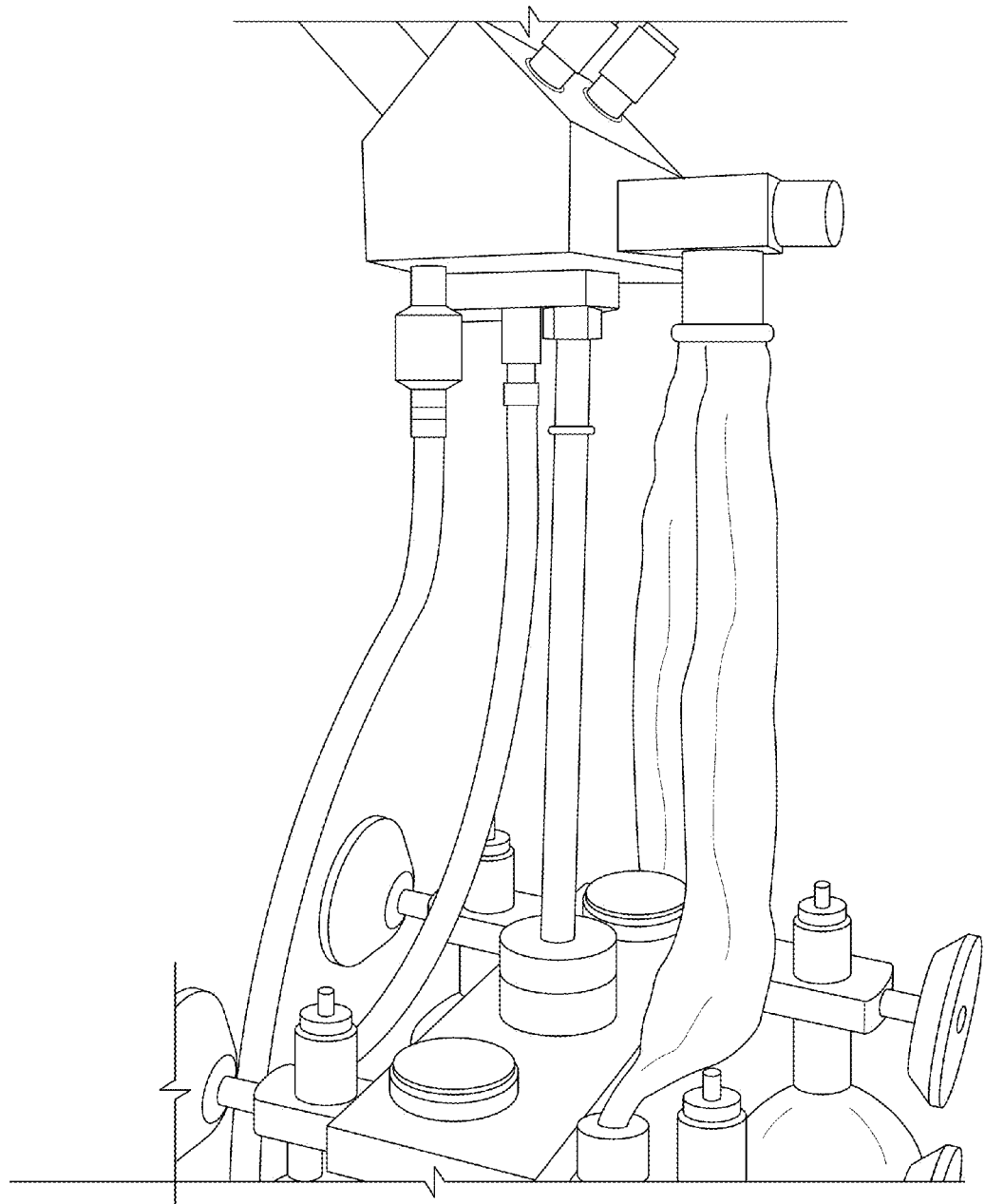
FIG. 7 is a prior art cart mounted nitrous oxide anesthetic administration system of FIG. 5.
Figure 8:
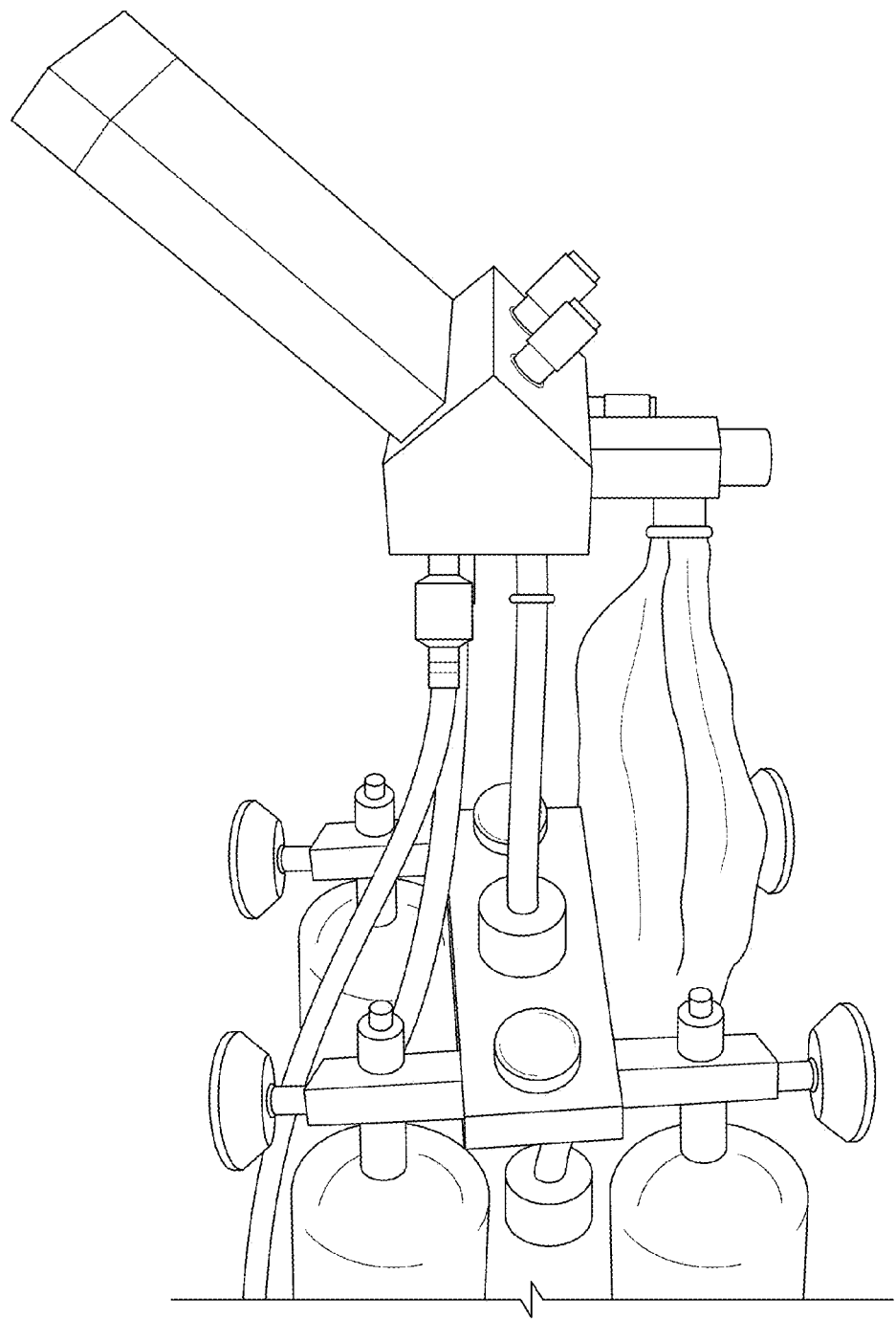
FIG. 8 is a prior art cart mounted nitrous oxide anesthetic administration system of FIG. 5.
Figure 9:
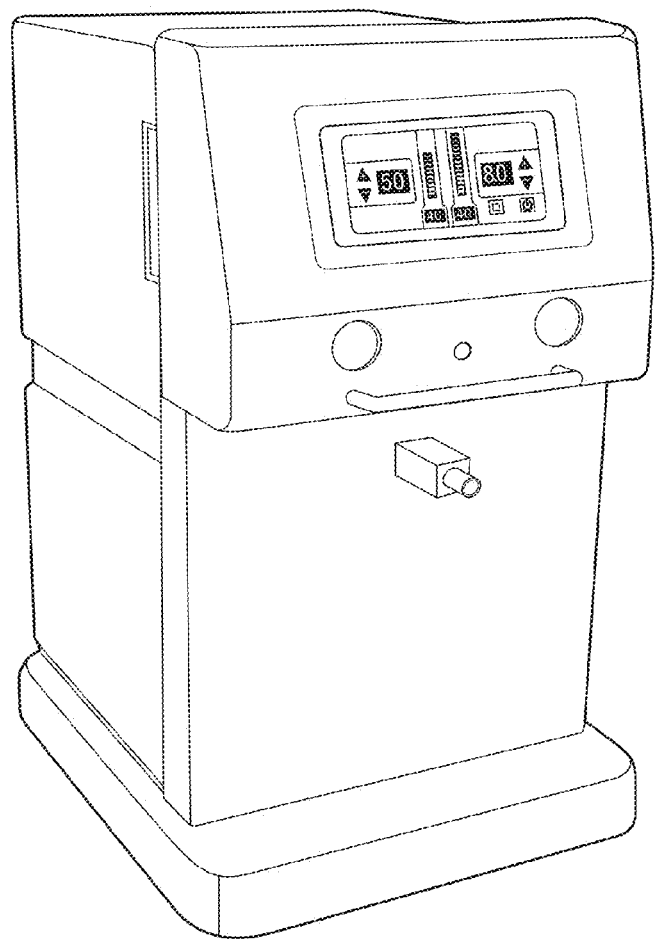
FIG. 9 is a prior art nitrous oxide anesthetic administration system.
Figure 10:
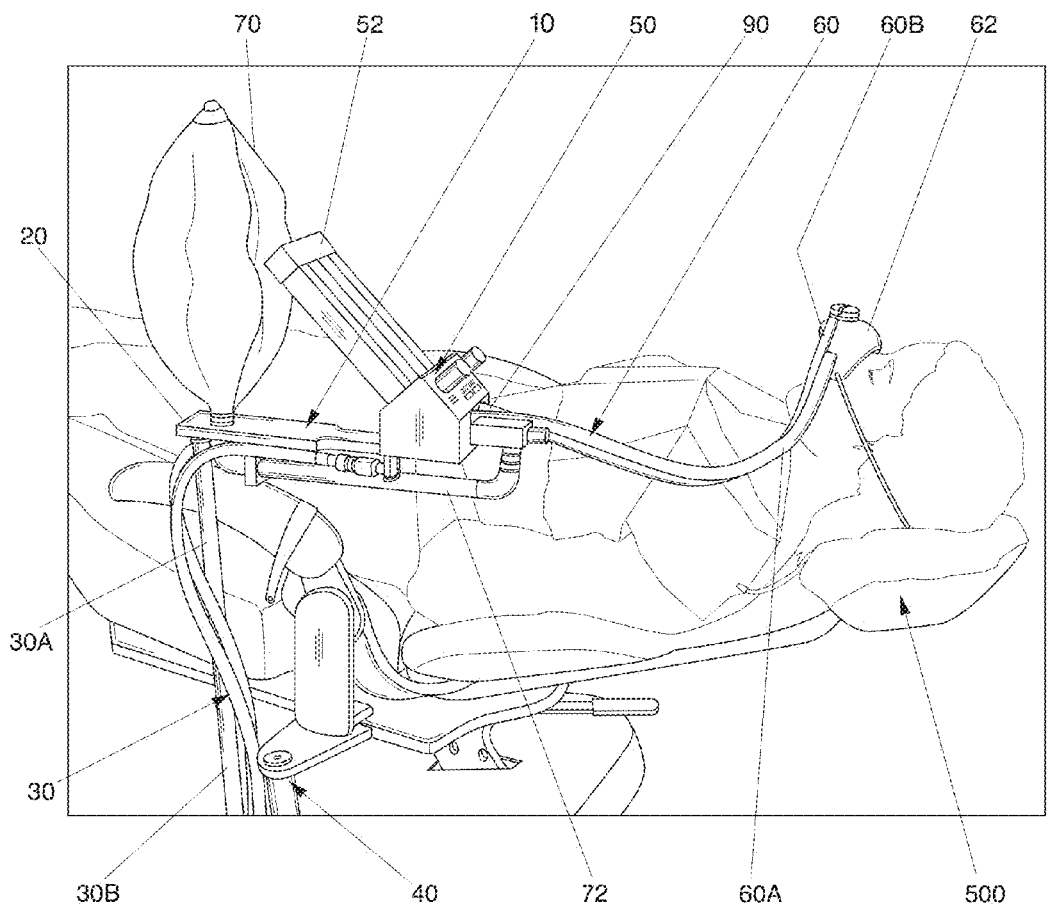
FIG. 10 is a left side view of the nitrous oxide anesthetic administration system of the present invention.
Figure 11:
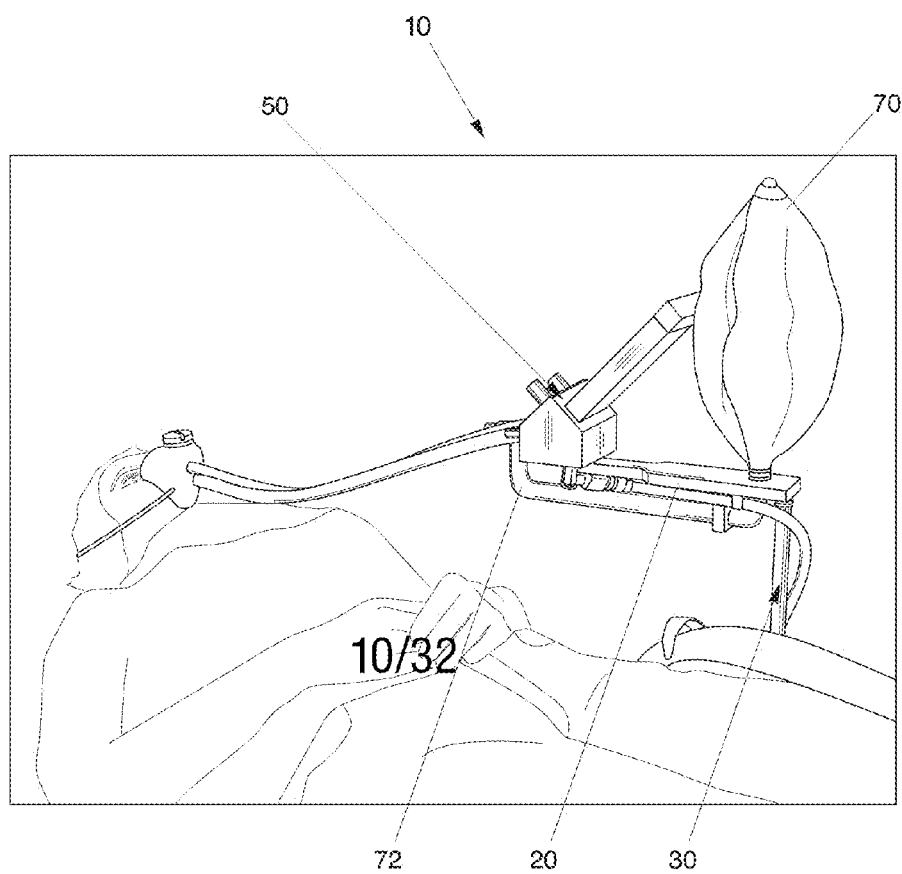
FIG. 11 is a right side view of the invention of FIG. 10.

Referring to FIGS. 10-19, a nitrous oxide anesthetic administration system 10 of the present invention is shown. The present invention is a nitrous oxide administration system 10 which provides convenient, direct access by a medical practitioner, a clear line of vision for the medical practitioner, and flexibility to accommodate the patient and medical professional's needs.

It should be understood that this invention is well suited and preferably used in a dental office environment; however, it may be used in any environment where delivery of objects to a work area is desired. The invention will be disclosed herein in connection with a dental office environment; however, the present invention is not intended to be limited to that particular use and may be used in any health care setting or any setting where a nitrous oxide is required. The configuration of the system components may vary depending on variations in the patient chair, physical site constraints and on the needs of a particular dental practice Most importantly, the nitrous oxide administration system 10 includes a mounting surface structure 20 and adjustable post mechanism 30 which is mounted directly to a patient chair 500 using a mounting plate assembly 40. A system for delivering nitrous oxide is attached to the mounting surface structure 20 or adjustable post mechanism 30 to provide convenient and direct access to the practitioner for delivering the nitrous oxide to the patient, which will be further explained herein.

The nitrous oxide anesthetic administration system may include some elements of prior art nitrous oxide delivery systems. For example, it may include a low-vacuum fluid generated by a vacuum source, a nitrous oxide fluid provided by a nitrous oxide source, and a scavenging mask. In addition, the nitrous oxide safety system may also include an oxygen source, mixing valve, flow meter, breathing bag, and tubing or lines. Note, the nitrous oxide anesthetic administration system of the present invention may also include elements of the system disclosed in "Nitrous Oxide Safety System" (Non-Provisional patent application Ser. No. 12/398,783 filed Mar. 5, 2009).

Referring to FIG. 1, the present invention is a system for administering nitrous oxide 10 which is preferably attached to a patient chair 500. The system generally includes: a mounting surface structure 20, a fluid control system 50 attached to the mounting surface structure 20, a nasal delivery interface system 60 connected to a patient and fluid control system 50, a nitrous oxide and oxygen supply (not shown) fluidly connected to the fluid control system 50, a vacuum source (not shown) for scavenging excess gases, a breather bag 70 fluidly connected to the fluid control system 50 and mounted to the mounting surface structure 20 in a vertical orientation, a mounting plate assembly 40 (FIG. 17) to interface with patient or dental chairs from multiple manufacturers, an adjustable post mechanism 30 attached to the mounting plate assembly 40 and the mounting surface structure 20, supply gas connectors 80A, 80B (FIG. 18) and mixed gas output connector 90 attached to the fluid control system 50, and other hardware, software, lines, and tubing that are necessary to administer nitrous oxide in a health care environment, preferably a dentist's office.

The system includes an adjustable post mechanism 30 attached to a patient or dental chair 500. The adjustable post mechanism 30 may include a cylindrical post 30A that is both pivotally and height adjustable within a corresponding sleeve 30B. The post 30A may slidably engage within the sleeve 30B and may be positioned in a fixed or temporary position when necessary. The post 30A may be secured into a position by use of methods known in the art including ratcheting mechanisms or a tightening collar. The adjustable post mechanism 30 is configured and arranged for height adjustment and pivotal adjustment to provide convenience of use to a practitioner.

Figure 17:
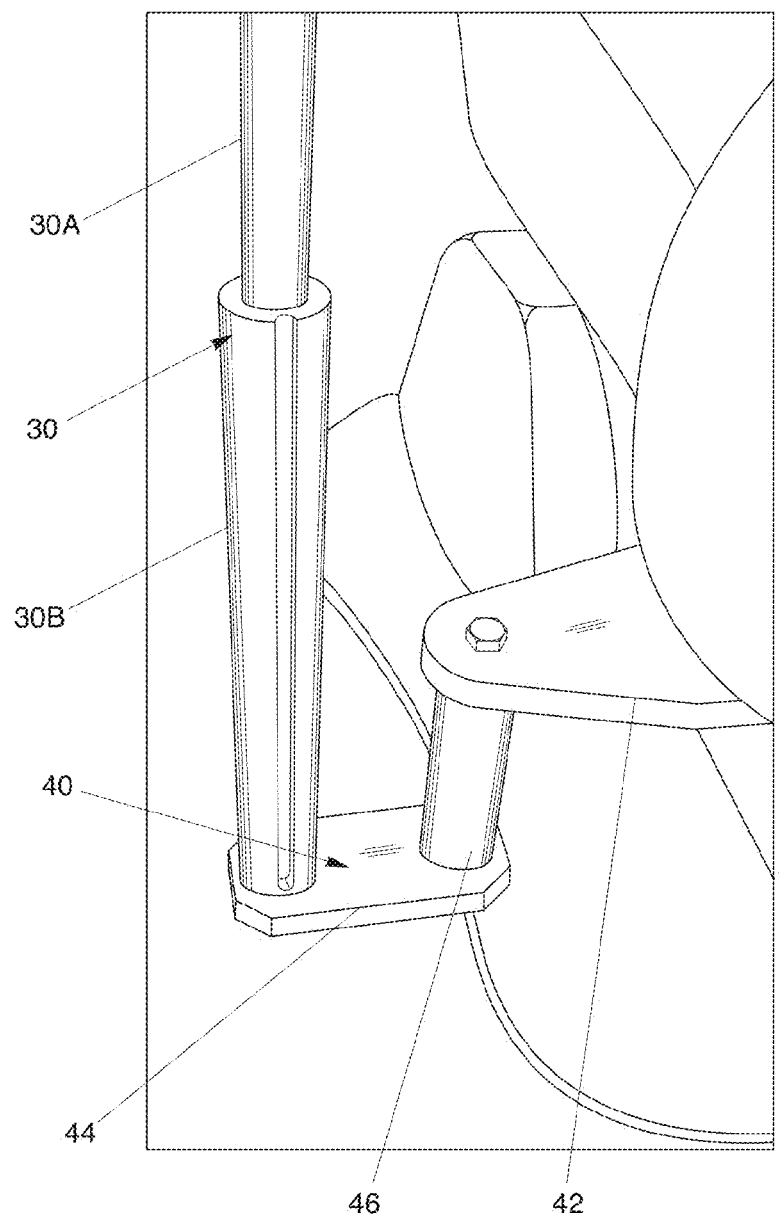
FIG. 17 is a close-up view of a bottom portion of the present invention.

The adjustable post mechanism 30 is attached to a mounting plate assembly 40 which is attached to a lower portion of a patient chair 500. Referring to FIG. 17, the mounting plate assembly 40 may include a chair attachment structure 42, a base plate 44, and a vertical extension structure 46 connecting the chair attachment structure 42 and the base plate 44. The base plate 44 defines an aperture for receipt of a bottom end of the adjustable post mechanism 30. The base plate 44 is attached to the adjustable post mechanism 30 with sufficient strength and can accommodate a wide range of adjustable post mechanisms 30. The base plate 44 lies along a horizontal axis. The chair attachment structure 42 is connected or attached to a bottom or lower portion of a patient chair 500 at a proximal end. The chair attachment structure 42, at the distal end, attaches to an extension structure 46 using methods known in the art. The extension structure 46 attaches to the chair attachment structure 42 and the base plate 44. In one embodiment, the extension structure 46 extends downwardly from the chair attachment structure 42 and is secured, at a top end, to the chair attachment structure 42 using a bolt or other fastener. The base plate 44 then attaches to a bottom end of the extension structure 46. Once the chair attachment structure 42, extension structure 46, and base plate 44 are secured to one another, they form a mounting plate assembly 40 for possible adaptation to other chairs made by various manufacturers. It should be noted that the mounting plate assembly 40 may interface with a variety of patient chairs 500A-E from multiple manufacturers as illustrated in FIG. 16.

The mounting surface structure 20 includes a top surface and a bottom surface. The bottom surface of the mounting surface structure 20 is attached to a top end of the adjustable post mechanism 30. The mounting surface structure 20 is positioned along a horizontal axis or approximately 180 degrees. The mounting surface structure 20 is attached to the breather bag 70 at a proximal end and a fluid control system 50 at a distal end closest to a practitioner.

Figure 14:
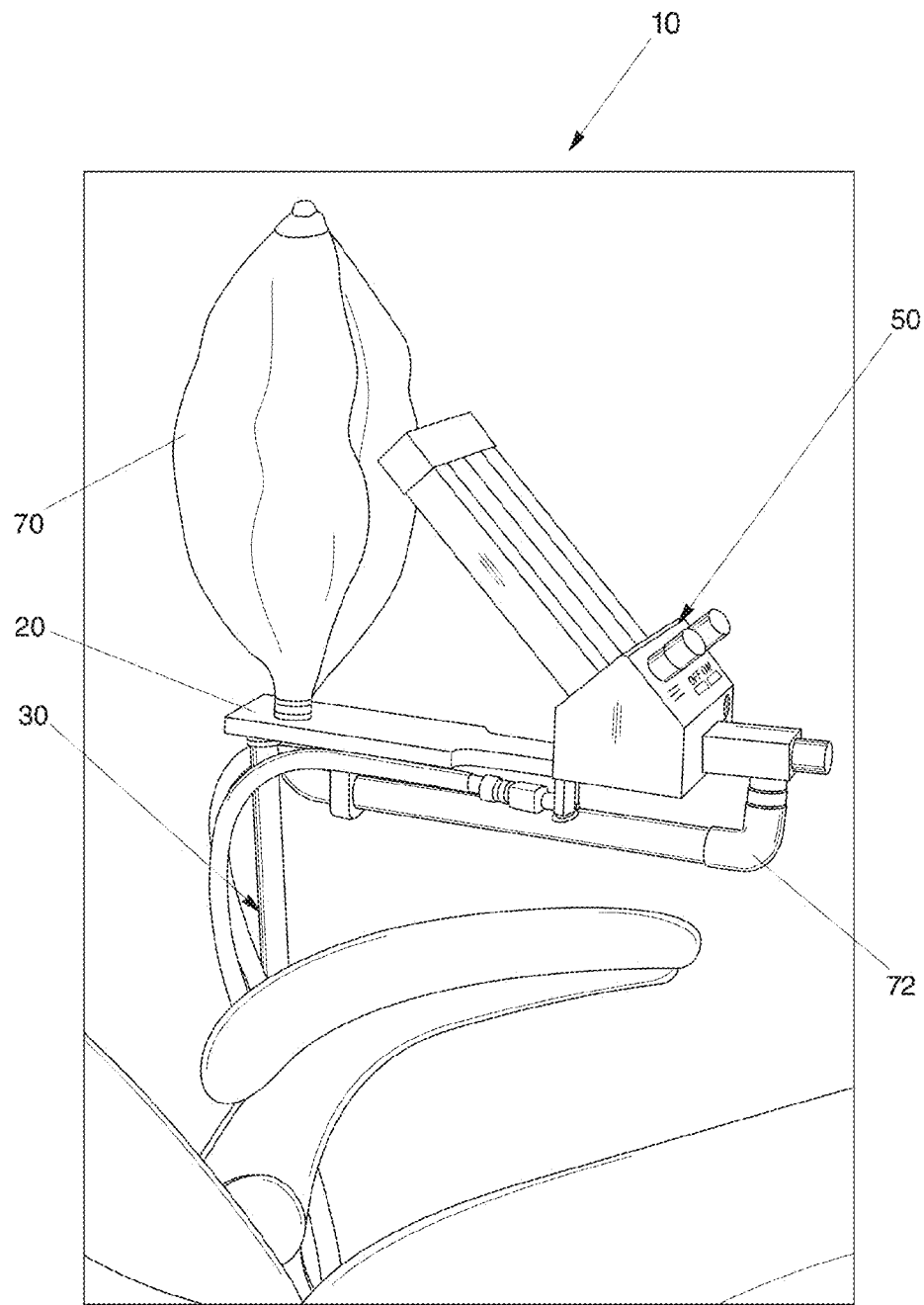
FIG. 14 is a left side view of the invention of FIG. 10.
Figure 18:
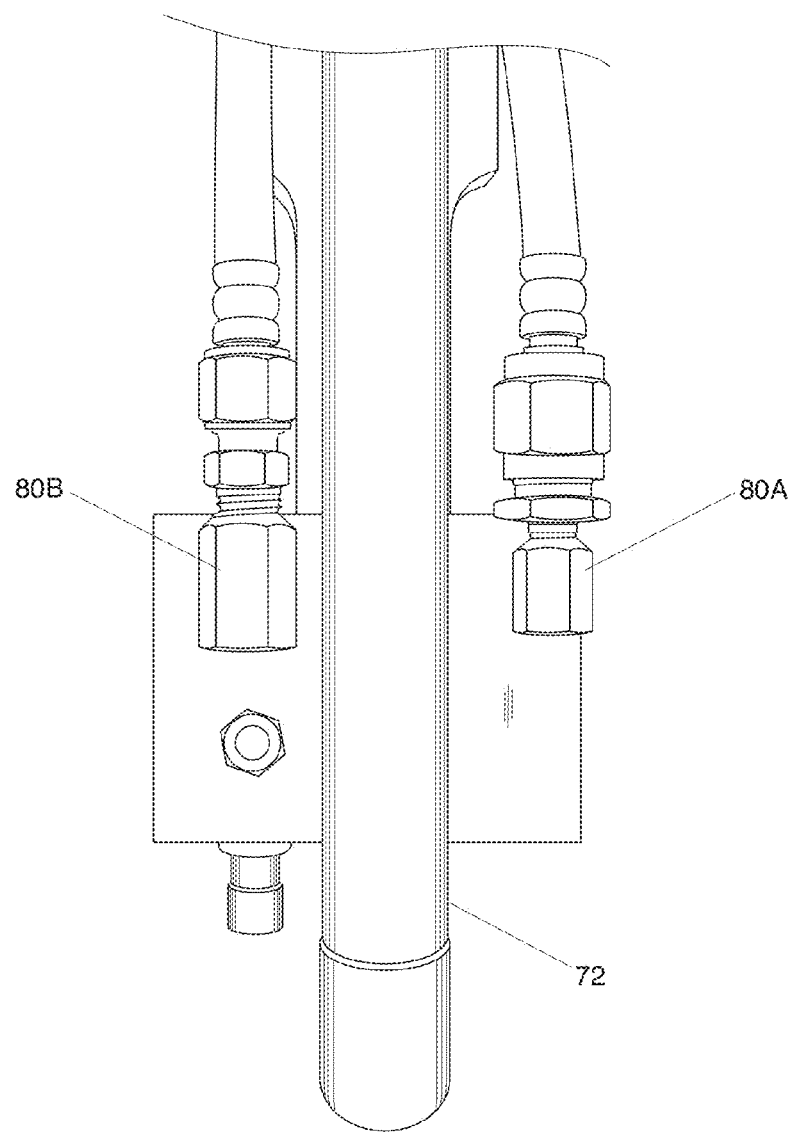
FIG. 18 is close-up view of gas connectors used with the present invention.
Figure 19:
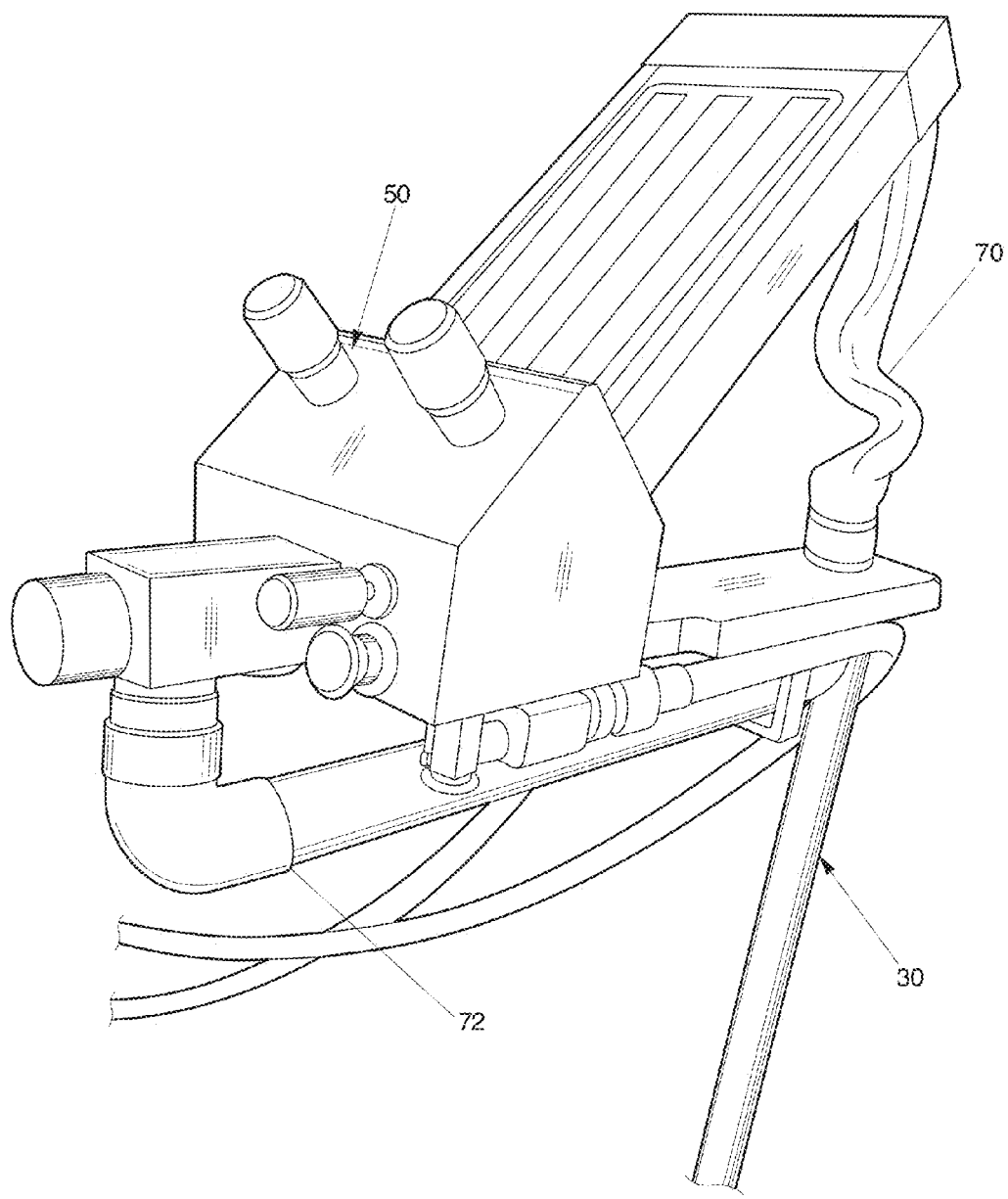
FIG. 19 is a front perspective view of the present invention.

Referring to FIGS. 14 and 19, a fluid control system 50 for controlling the flow of nitrous oxide and oxygen is attached to the mounting surface structure 20. The fluid control system 50 includes a fluid flow meter 52 mounted on a top surface of the fluid control system 50. A display of the fluid flow meter 52 is positioned along a vertical axis at less than 90 degrees, preferably between 30 degrees to 45 degrees, relative to the mounting surface structure 20 to provide a better view to the practitioner. Referring to FIG. 18, the nitrous oxide and oxygen supply (not shown) is fluidly connected to the fluid control system 20 using fluid connectors 80A, 80B fixedly attached to the bottom surface of said mounting surface structure 20. The fluid control system 50 also includes an emergency air intake port.

Figure 12:
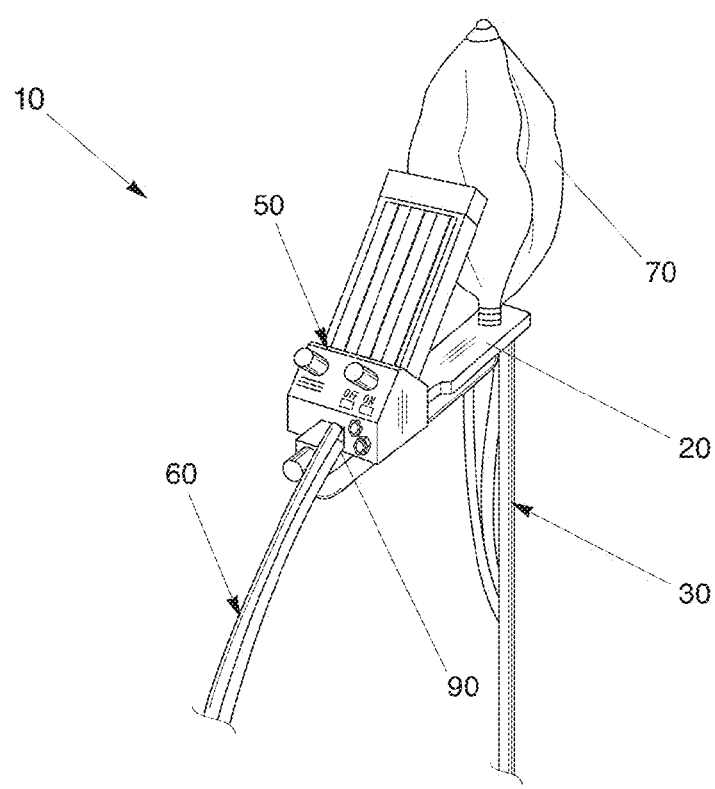
FIG. 12 is front perspective view of the invention of FIG. 10.
Figure 13:
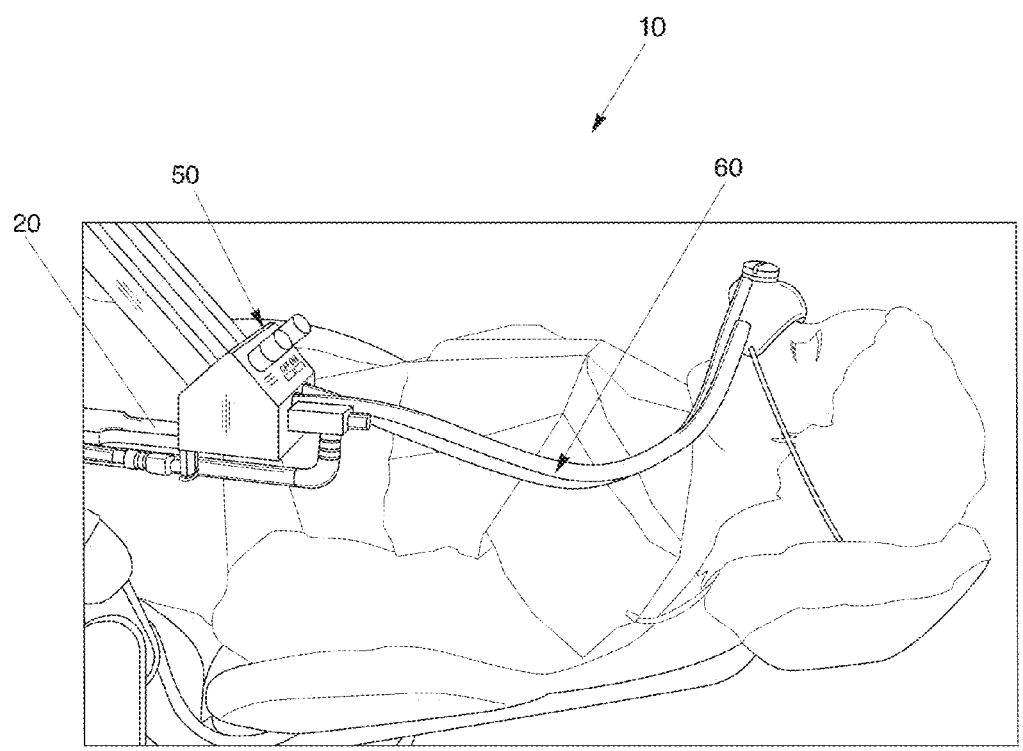
FIG. 13 is a partial left side view of the invention of FIG. 10.

Referring to FIGS. 12-13, a nasal delivery interface system 60 is fluidly connected to the fluid control system 50. The nasal delivery interface system 60 includes a single scavenging tube 60B and a single nitrous oxide and oxygen tube 60A fluidly connected to a single nasal delivery mask 62. The fluid control system 500 including a mixed gas output connector 90 fluidly connected to the single nitrous oxide and oxygen tube 60A. A vacuum source (not shown) is fluidly connected to the single scavenging tube 60B for scavenging excess gases and the fluid control system 50. Note, the vacuum source may be provided by a variety of methods known in the art.

Figure 15:
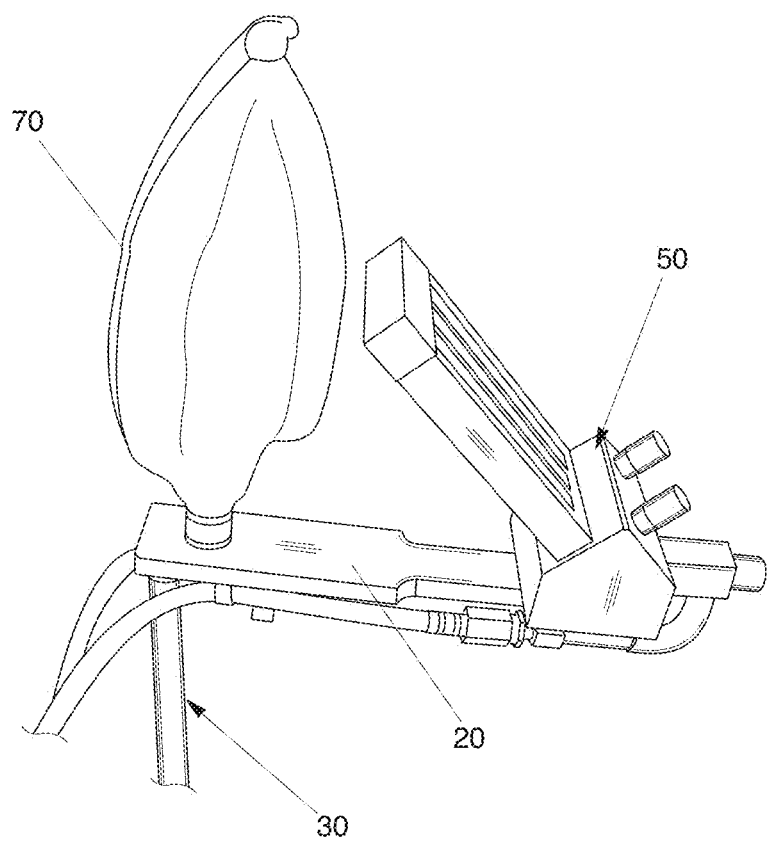
FIG. 15 is a rear perspective view of the invention of FIG. 10.
Figure 16A:
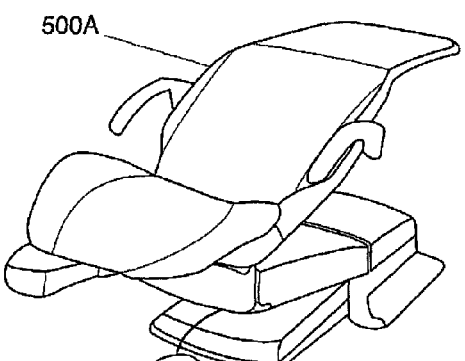
FIG. 16A-16E are a sample of prior art dental chairs which can be utilized with the present invention.
Figure 16B:
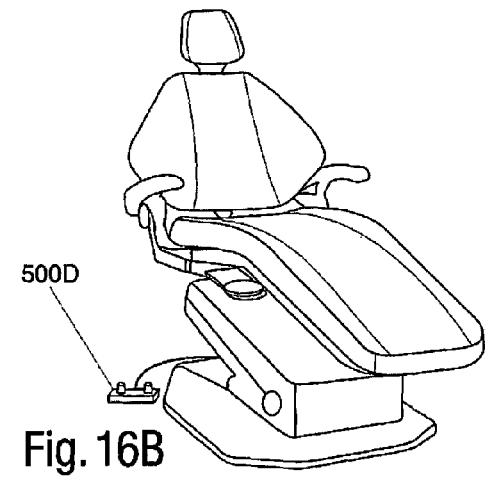
Figure 16C:
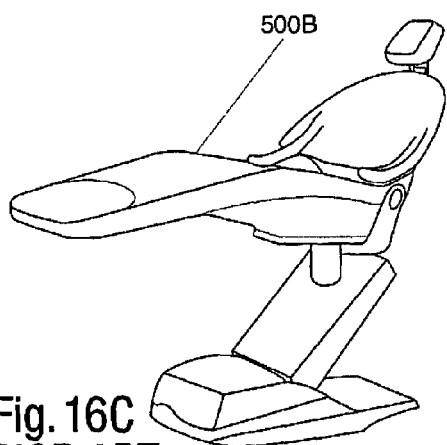
Figure 16D:
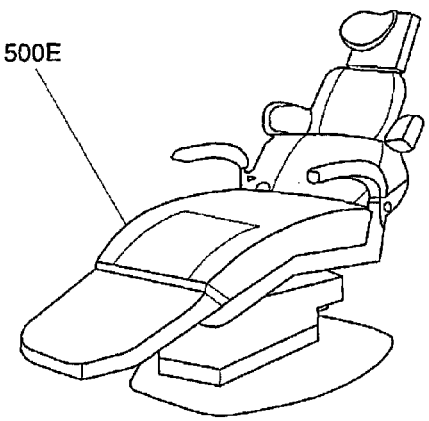
Figure 16E:
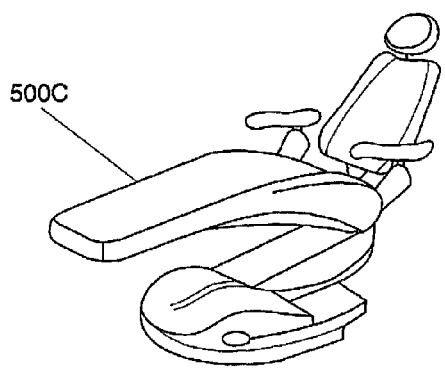

Referring to FIG. 15, the breather bag 70 is vertically mounted to a top surface of the mounting surface structure 20. The breather bag 70 is positioned along a vertical axis or about 90 degrees depending upwardly from the mounting surface structure 20. The breather bag 70 is mounted rearward or behind the fluid control system 50 to allow full view of fluid flow meter display 52. The breather bag 70 is fluidly connected to the control system 50 by way of an elongated tubular structure 72 attached to a front surface of the fluid flow meter 52.

In operation, the present invention provides a system for administering anesthesia/analgesia gas 10 or any type of gases which provides convenient and direct access to a medical practitioner. The practitioner connects the nasal delivery interface system 60 to the patient and to the fluid control system 50. After the nasal mask 62 is attached to the patient, the nitrous oxide/oxygen gas, or anesthetic, is turned on and the gas enters a single tube 60A fluidly connected with the nasal delivery mask 62. Throughout the administration of the gas, the system 10 allows the practitioner a direct view and a close proximity to the upright breathing bag 70, fluid control system 50 including display 52, patient, and all other parts of the nitrous oxide administration system 10 which makes the administration of the gas much more efficient, safe, and less time consuming. Also, the mounting of the nitrous oxide anesthetic administration system 10 to a patient's chair provides greater stability and convenience to a practitioner.

In summary, the present invention provides a system for administering anesthesia/analgesia gas 10 which provides convenient, direct access by a medical practitioner, a clear line of vision for the medical practitioner, and flexibility to accommodate the patient and medical professional's needs. The present invention is a novel configuration which mounts the control system, monitoring devices, safety devices and breather bag which mounts directly or indirectly to the patient chair.

Some of the benefits of the proposed novel invention are as follows. The present invention shortens hoses from the fluid control system to the patient to reduce cost, complexity and weight. The present invention minimizes control input to nasal delivery interface device output (latency) by at least 50% by shortening hose length. The present invention minimizes patient head access limitation and movement restriction by minimizing hose lengths, stiffness and multiples. The present invention eliminates dual hoses for each of: O2/N2O and scavenge. The present invention puts controls within direct, forward reach of doctor (from normal treatment position) throughout procedure. The preset invention puts displays and gauges in direct view of doctor and assistant throughout procedure to enhance practitioner and patient safety. The present invention provides open passage around patient and patient support chair by eliminating support cart. The present invention provides open passage around patient and patient support chair by eliminating tubing crossing passageways. The present invention eliminates potential of toppling cart and damaging systems by eliminating tubing crossing passageways. The present invention eliminates the potential danger caused by damaging a high pressure gas system. The present invention maximizes visibility of breather bag by doctor and assistant throughout procedure by orienting breather bag, or bellows, superior to inlet rather than current designs which hang breather bags inferior to their inlet. The present invention reduces patient anxiety prior to their procedure by reducing the visual impact of the anesthetic apparatus. The present invention minimizes system size, complexity and cost. The present invention has system configuration adaptable to all operatory configurations. The present invention has a system capable of mounting to most commercially available patient chairs via model specific interface plates. Most importantly, the present invention mounts directly to the patient chair to accomplish all of the above.

Figure 20:
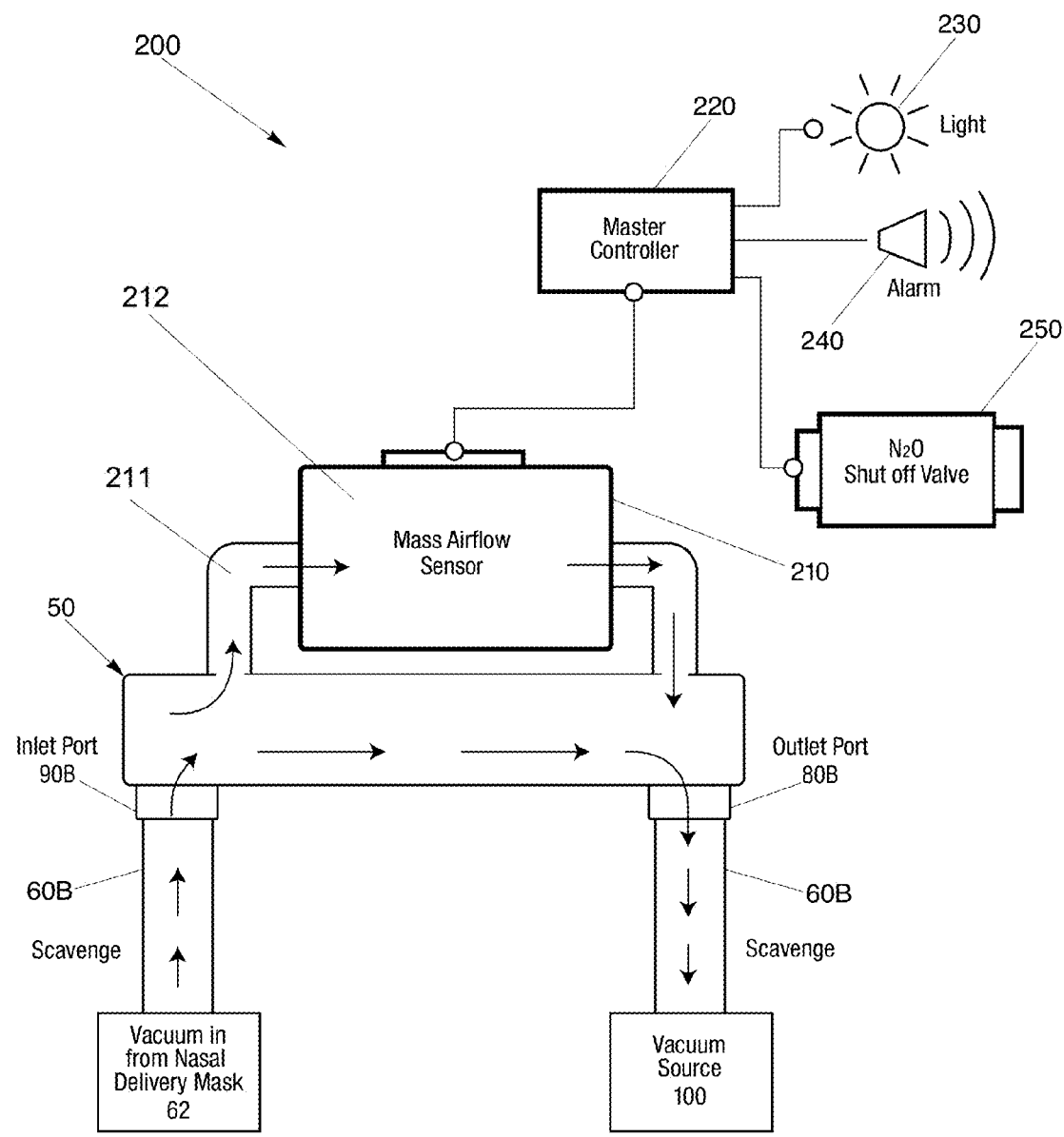
FIG. 20 is a schematic illustration of another embodiment of the present invention which includes a safety scavenging system.
Figure 21:
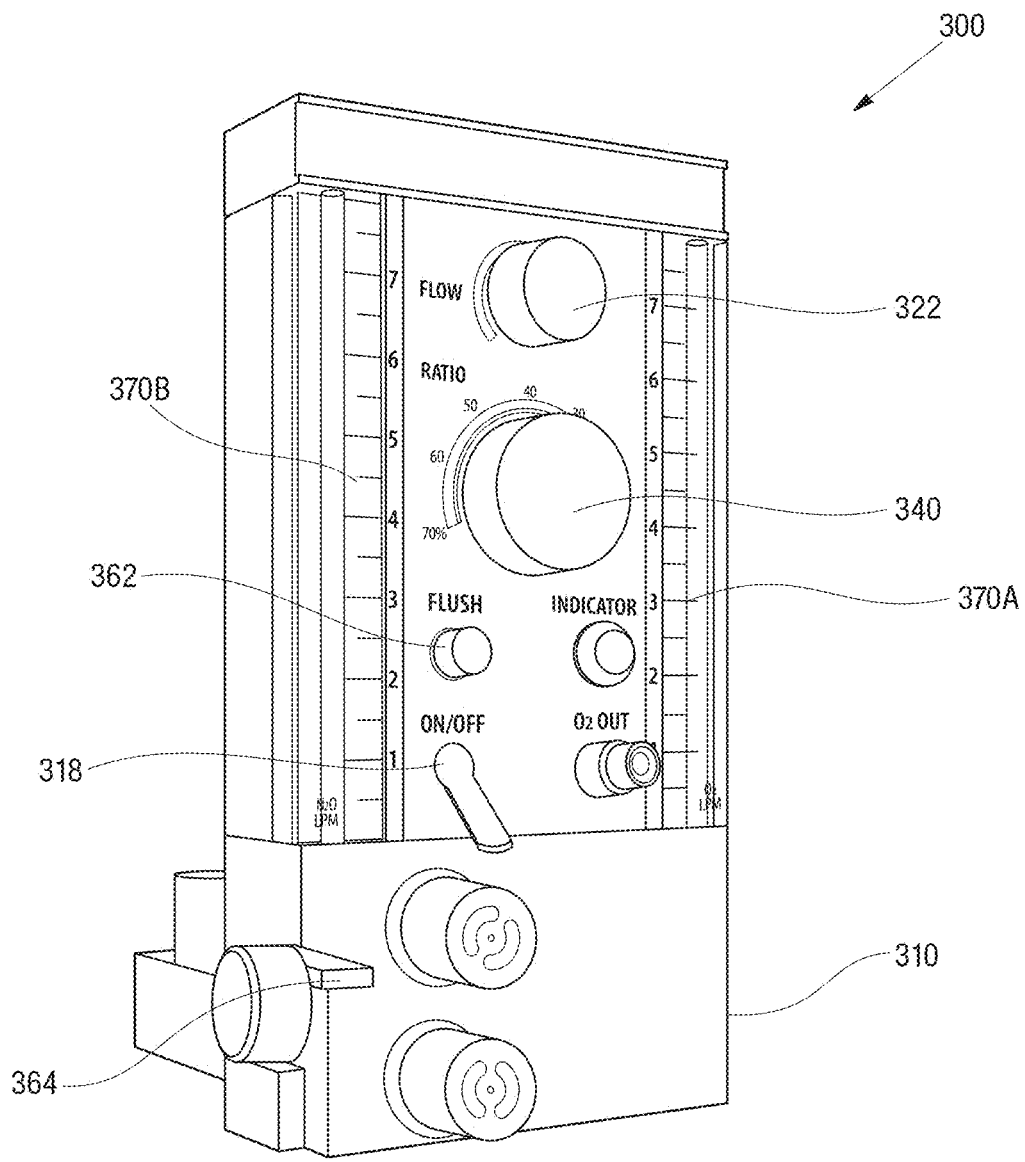
FIG. 21 is a perspective view of a preferred embodiment of the fluid control system of the present invention.
Figure 22:
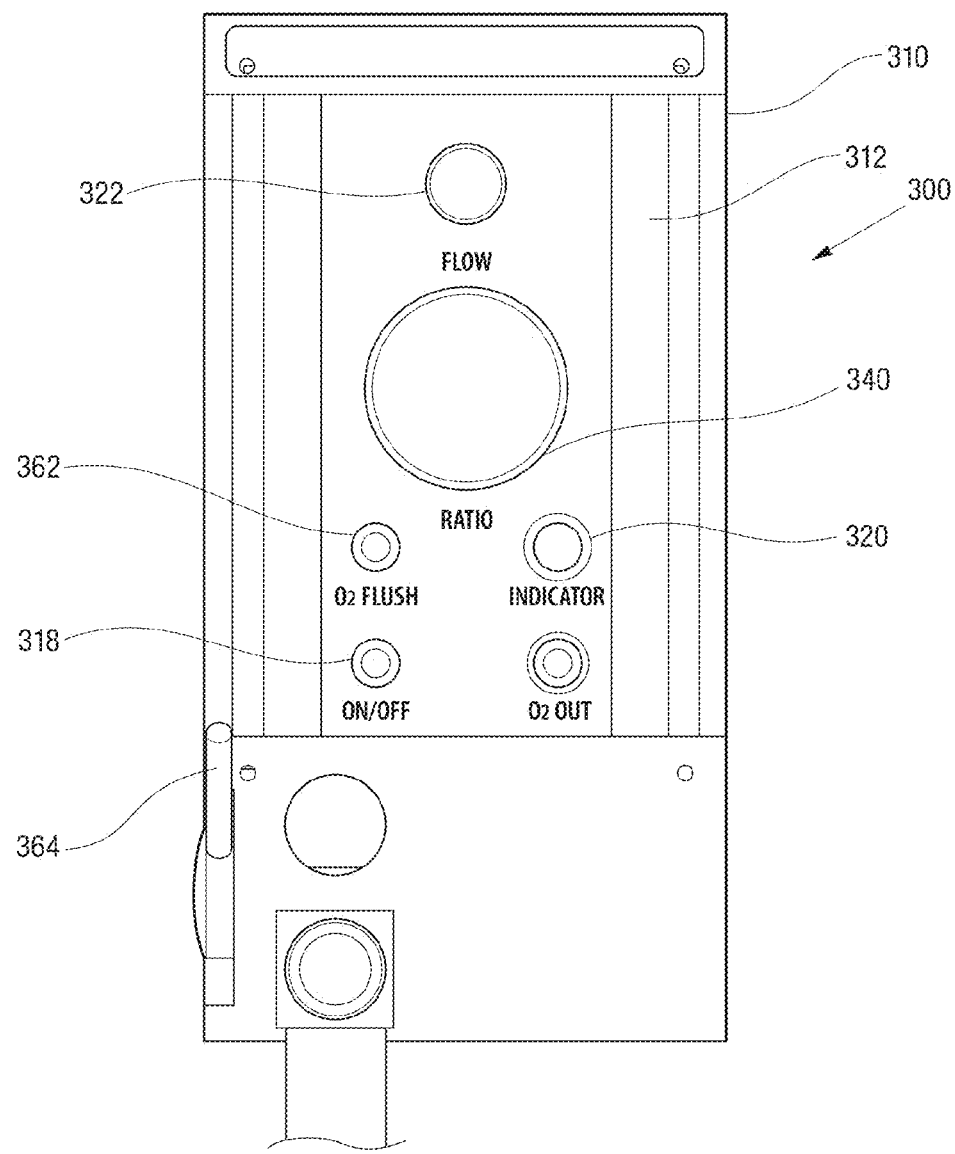
FIG. 22 is a front view thereof, showing the control layout.
Figure 23:
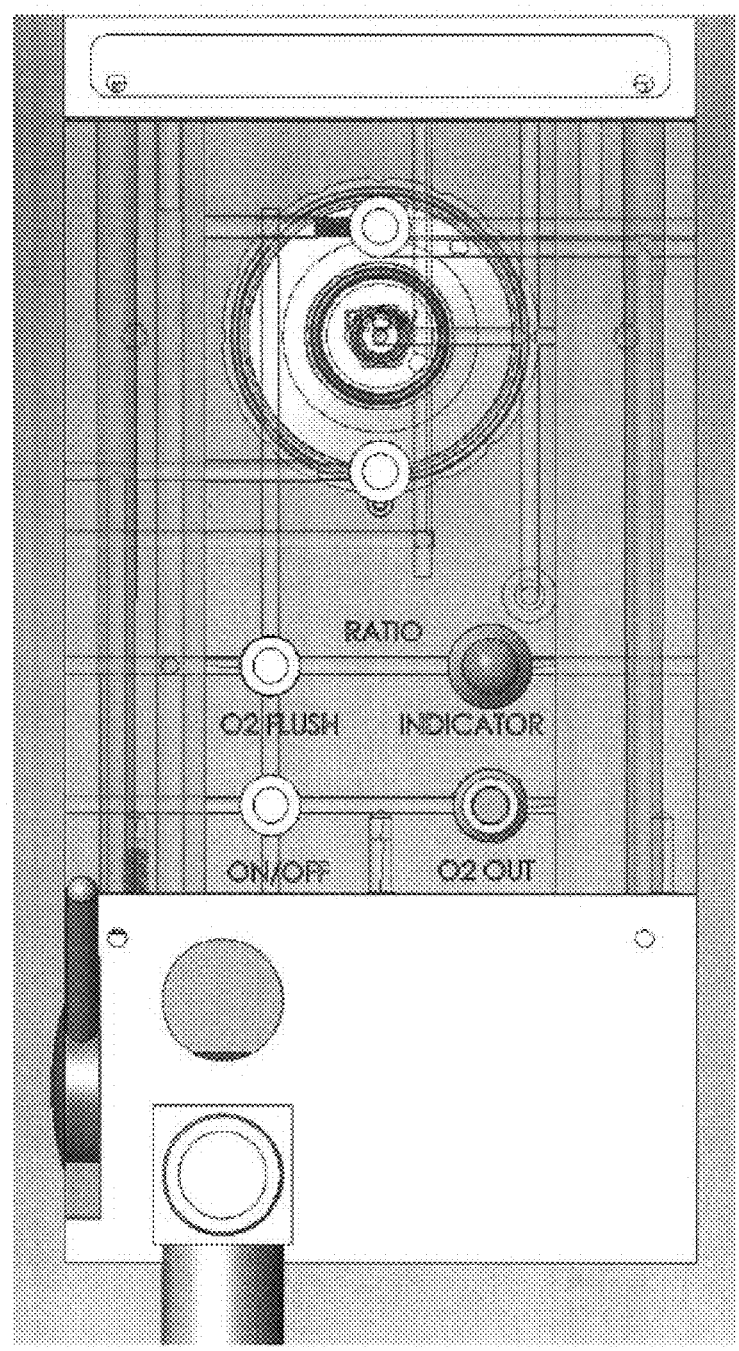
FIG. 23 is a front view thereof, showing main body bores within the flow meter.
Figure 24:
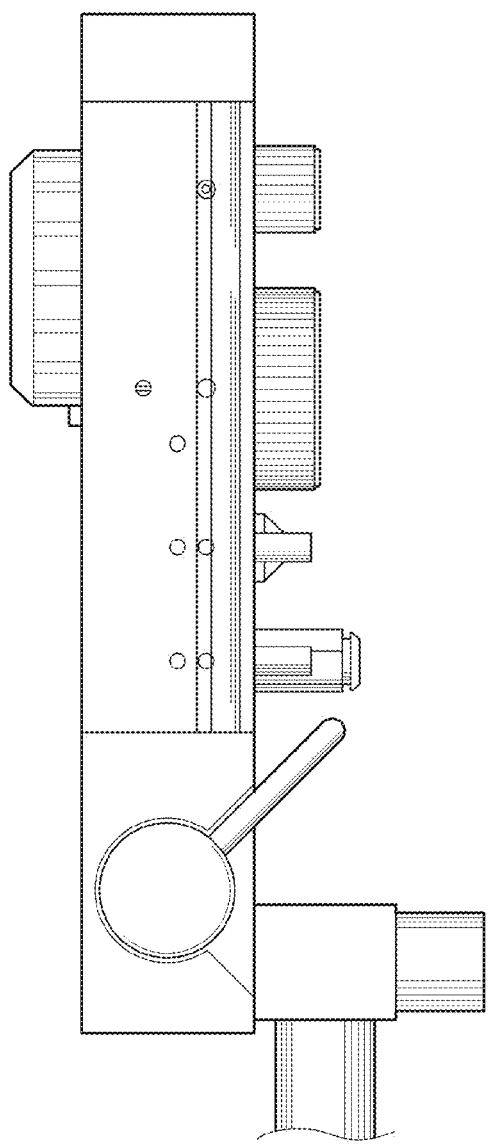
FIG. 24 is a left view thereof, with the conventional outlet manifold, bag down, 22 mm outlet.
Figure 25:
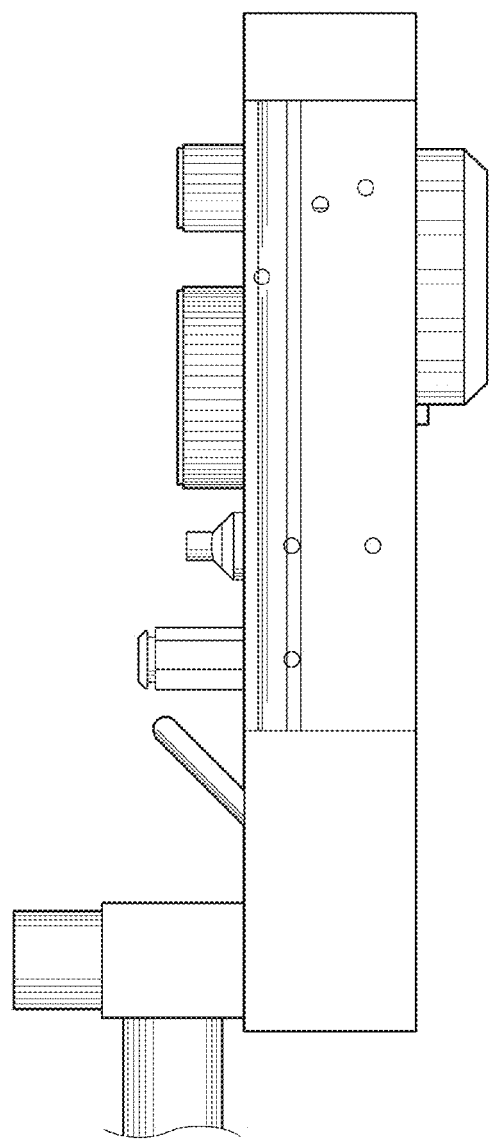
FIG. 25 is a right view thereof.
Figure 26:
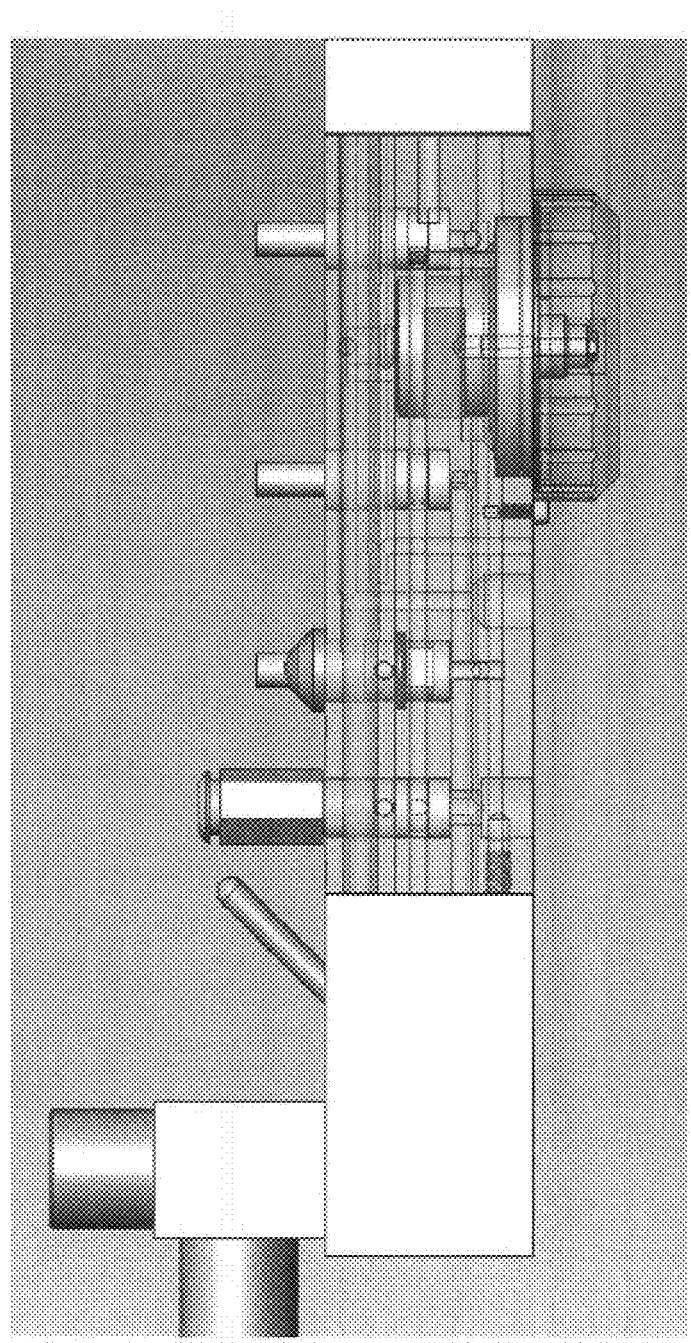
FIG. 26 is a left view thereof, showing the main body bores.
Figure 27:
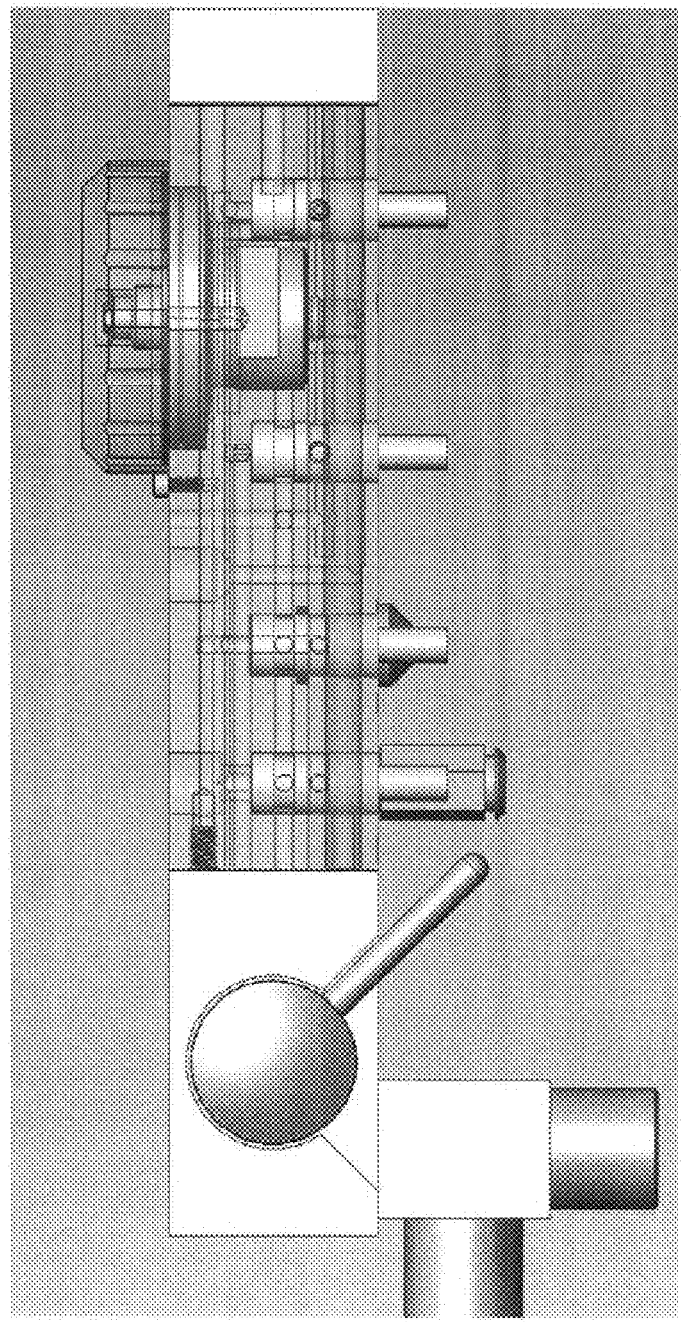
FIG. 27 is a right view thereof, showing the main body bores.
Figure 28:
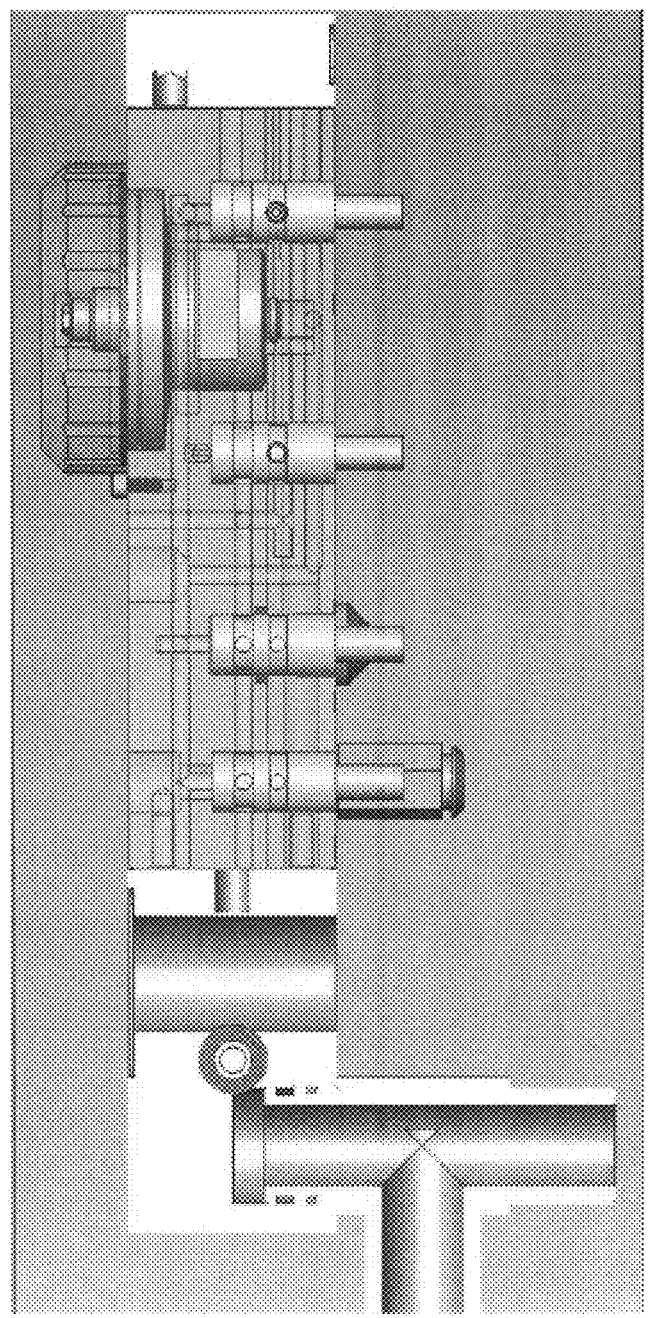
FIG. 28 is a left view thereof, showing a cross-sectional view through the A-B outlet switch.
Figure 29:
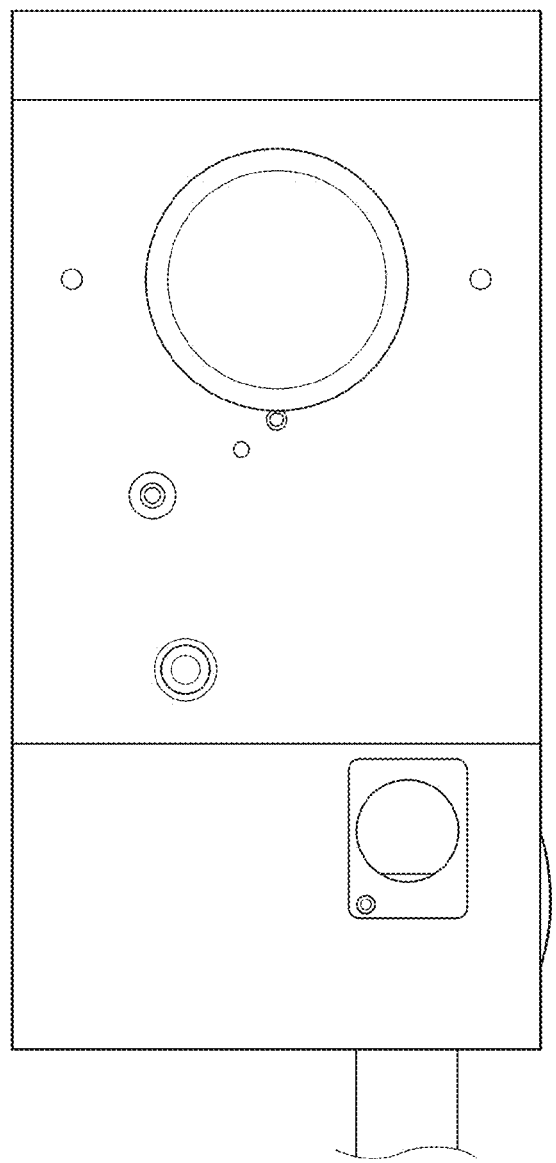
FIG. 29 is a rear view thereof.

Now referring to another embodiment of the present invention as schematically illustrated in FIG. 20 which includes a fluid control system 50 having a safety scavenge system 200. The safety scavenge system 200 includes a mass airflow sensor 210, master controller 220 which includes a CPU or processor, nitrous oxide valve 250, and various alarms 230, 240. The mass airflow sensor 210 reads the scavenging vacuum pressure which it communicates to the master controller 220. Depending upon the scavenging vacuum pressure and a set of predetermined ranges, the master controller 220 can activate an audio alarm 240, visual alarm 230, or shut off the nitrous oxide valve 250. In operation, the present invention provides a system for administering anesthesia/analgesia gas which prevents excessively high volumes of exhaled nitrous oxide in the operatory environment through monitoring of the scavenge vacuum pressure.

The safety scavenge system 200 more specifically includes the following components. It should be noted that the safety scavenge system 200 may be available within the fluid control system 50 as an internal component or as a standalone unit attached between the flow meter nitrous oxide inlet and nitrous oxide gas source or supply. The mass airflow sensor 210 for reading scavenging vacuum pressure is fluidly connected to the scavenging tube 60B before the vacuum source 100. The master controller 220, including a CPU or processor, in electrical communication with the mass airflow sensor 210 for receiving the scavenging vacuum pressure reading from the mass airflow sensor 210 which is compared to a predetermined range.

In one embodiment, the predetermined range is related to the American Dental Association's recommended 45 LPM (liters per minute) scavenge vacuum when nitrous oxide is in use. Typically, if scavenge pressure falls below the 45 LPM, it will trigger a light or visual alarm (less than 45 LPM), audio or audio/visual alarm (less than 25 LPM), or the nitrous oxide flow will be stopped (less than 15 LPM). Of course, these predetermined ranges as a triggering point may be adjusted according to the user's preferences including activating or deactivating certain responses.

In FIG. 20, a portion of vacuumed gas 211 is diverted through the mass airflow sensor. At 212, when the mass flow sensor reads less than 45 LPM, a light will flash and stay lit. At 212, when the mass flow sensor reads less than 25 LPM, an alarm will go off. At 212, when the mass flow sensor reads less than 15 LPM, N2O flow will be stopped.

A visual alarm 230 is in electrical communication with the master controller 220 which instructs the visual alarm 230 to activate if the scavenging vacuum pressure is less than a first predetermined range. An audio alarm 240 or audio/visual alarm is in electrical communication with the master controller 220 which instructs the audio alarm 240 to activate if the scavenging vacuum pressure is less than a second predetermined range. A nitrous oxide valve 250 is fluidly connected to the nitrous oxide supply and in electrical communication with the master controller 220 which shuts off the nitrous oxide shut-off valve 250 when the scavenging vacuum pressure is less than a third predetermined range.

One example of a configuration of the safety scavenge system 200 is illustrated in FIG. 20. The scavenge hose 60B is connected between the nasal mask or hood and the inlet port 90B of the fluid control system 50. A dental vacuum is plugged into the outlet port 80B. A portion of the flow is diverted through a mass airflow sensor valve 210. The electrical output of the mass airflow sensor 210 is sent to a processor or master controller 220 where it is calibrated at LPM flow. In operation, the processor output will turn on a warning light 230 when the flow falls below 45 LPM. An alarm 240 sounds when flow falls below 25 LPM. The nitrous oxide valve is shut off when the flow falls below 15 LPM.

In addition, the present invention includes the following method for administering nitrous oxide to a patient. First, a fluid generated by a vacuum source is provided. Second, nitrous oxide fluid from a nitrous oxide source is provided. Third, a means for scavenging excess nitrous oxide is in fluid connection with the nitrous oxide source and the vacuum source. Fourth, a safety scavenge system is connected to the fluid connection between the nitrous oxide source and the vacuum source. The safety scavenge system includes a mass airflow sensor, master controller, alarm, and nitrous oxide valve. Fifth, the means for scavenging excess nitrous oxide is connected to the vacuum source and the nitrous oxide source onto a patient. Sixth, a flow rate flow rate of the vacuum source is increased to provide fluid into the safety scavenge system. Seventh, nitrous oxide is released through the safety scavenge system upon the vacuum source reaching a predetermined range. Eighth, excess nitrous oxide is retrieved from the means for scavenging excess nitrous oxide using the vacuum source. Ninth, the vacuum source is decreased below the third predetermined range which prevents the safety control valve from releasing nitrous oxide. The safety scavenge system actuated by flow fluids to control the release of nitrous oxide therethrough.

The present invention also provides a configuration for fluid control system 300. Generally, the fluid control system 300 allows a user to adjust the flow of two fluids (in this application, gases) through the fluid control system. Oxygen and nitrous oxide at 50 psi are plumbed to input ports on the back of the flow meter housing of the fluid control system. The user turns an on/off switch to the "on" position, and adjusts the flow of the oxygen to allow oxygen to create variable pressure at a differential pressure regulator. Sufficient pressure of the oxygen in the differential pressure regulator allows nitrous oxide to flow through the differential pressure regulator. After the nitrous oxide passes through the differential pressure regulator, its flow is regulated by a ratio adjustment valve. The two output conduits (one for oxygen, and one for nitrous oxide) are combined in a combined outlet conduit. The combined gas can be then provided to a patient.

The fluid control system has a flow meter housing 310 that shows the relative flow of gases such as oxygen and nitrous oxide through the fluid control system. The fluid control system can also provide automatic shutoff mechanisms that prevent flow of a second gas (such as nitrous oxide) when there is insufficient flow of a first gas (such as oxygen), or when there is insufficient vacuum pressure in the scavenge system. The exemplary embodiment of the fluid control system 300 is shown in FIGS. 21-32.

The exemplary embodiment of the fluid control system 300 has a substantially rectangular housing 310, which has a front face 312 that supports controls and a display so that a user can observe the operation of the fluid control system, activate the fluid control system, and adjust the flow of gases through the fluid control system. The exemplary embodiment is configured to control the flow of two gases, and to combine the two gases before the gases exit the fluid control system.

FIGS. 21-29 show the preferred configuration of the fluid control system housing 310. The operation of the fluid control system is best understood with reference to FIGS. 30-32, which show schematics of three fluid control systems according to the present invention. The schematics more clearly show how the features of the housing interact.

The exemplary embodiment of the fluid control system has a first intake conduit 314 and a second intake conduit 316. The first intake conduit 314 can be connected to a first gas supply, such as a tank (not shown). The second intake conduit 316 can be connected to a second gas supply, such as a tank (not shown).

The fluid control system 300 can be turned on an off by a shutoff valve 318 positioned along the first intake conduit 314. A user can move the shutoff valve 318 between an off position in which the valve does not permit gas to flow through the first intake conduit 314 beyond the shutoff valve 318, and an on position in which the valve 318 permits gas to flow through the shutoff valve. As will become apparent below, when there is no gas flow through the first intake conduit, there will be no gas flow through the second intake conduit. In the exemplary embodiment, the first gas is oxygen, and the second gas is nitrous oxide. Thus, but stopping the flow of oxygen in the first intake conduit of the flow meter, the user can stop the flow of nitrous oxide in the second intake conduit of the fluid control system.

Preferably, there is an oxygen flow indicator on the fluid control system. In the exemplary embodiment, there is a light 320 on the front of the housing that is lit when oxygen is flowing through the first intake conduit 314. The light is off when oxygen is not flowing through the first intake conduit.

After a user has turned the fluid control system 300 on by moving the shutoff valve 318 to the on position, and oxygen is flowing through the first intake conduit 314, the user can adjust the flow of oxygen in the fluid control system beyond the first intake conduit 314. A flow controlling valve 322 is positioned at a joint where the first intake conduit 314 is connected to the first output conduit 324. The valve 322 is movable from a closed position to an open position, and various positions in between, which allow varying amounts of oxygen to flow through the flow controlling valve. The first output conduit 324 is in fluid connection with the first intake conduit 314 by way of the flow controlling valve 322, and is in direct fluid connection with a combined output conduit.

Figure 30:
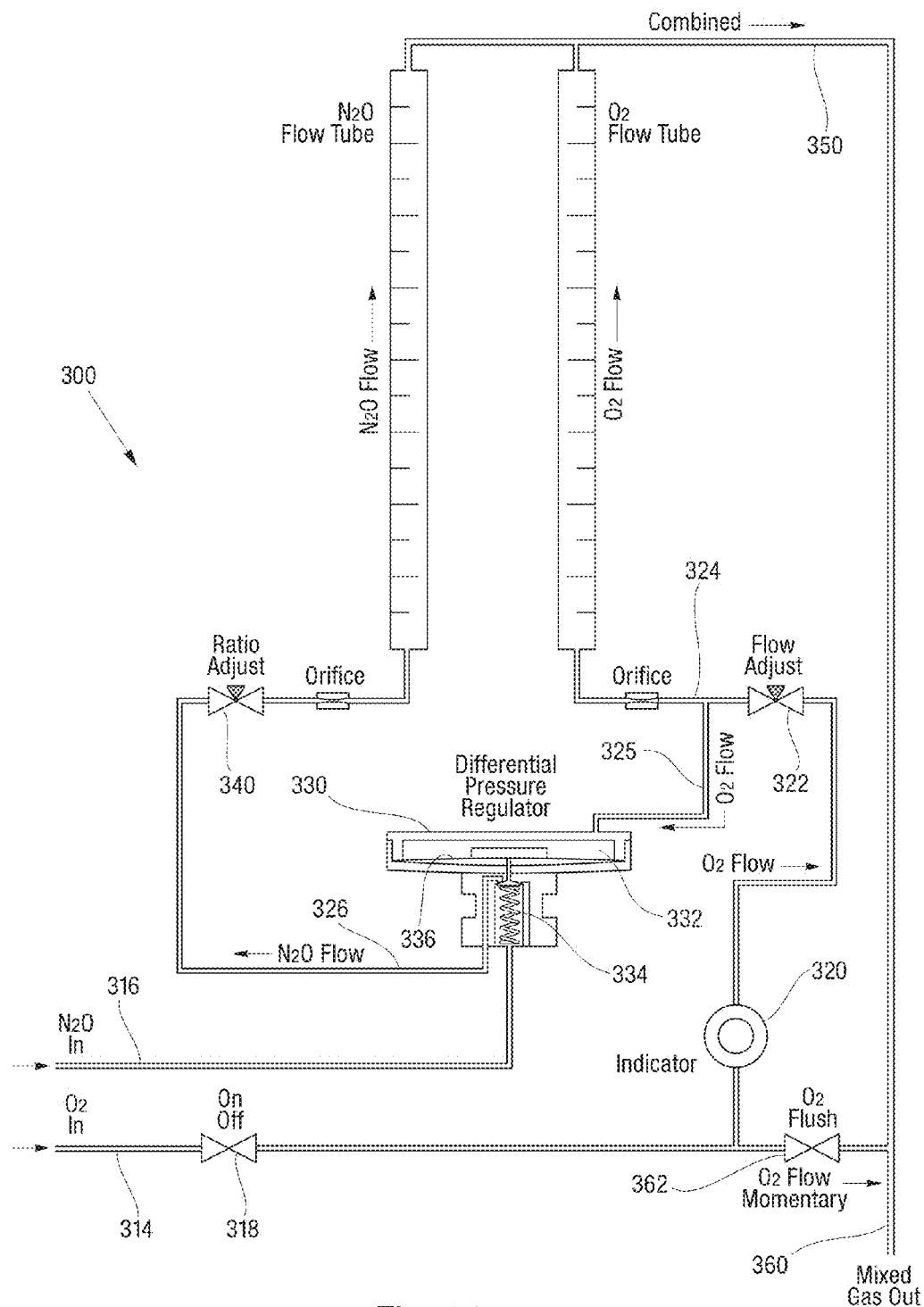
FIG. 30 is a schematic of the fluid control system.

The flow of oxygen through the first output conduit 324 can be used to open a differential pressure regulator 330, which allows nitrous oxide to flow from the second intake conduit 316 to the second output conduit 326. The differential pressure regulator 330 has a first chamber 332 and a second chamber 334. The first chamber 332 is fluidly connected to the first output conduit 324. In the exemplary embodiment, a regulator oxygen supply conduit 325 connects the first output conduit 324 with the first chamber 332 of the differential pressure regulator 330. The second chamber of the differential pressure regulator 330 is fluidly connected to the second intake conduit 316. A movable wall 336 separates the first and second chambers, and is spring biased to a closed position in which nitrous oxide cannot pass from the second chamber into a second output conduit. FIG. 30 shows the differential pressure regulator in the closed position. The wall 336 can be moved by increasing the pressure in the first chamber relative to the pressure in the second chamber. As oxygen flow is increased, pressure in the first chamber increases, and this pressure opposes the spring bias of the wall. When oxygen pressure in the first chamber is sufficiently greater than nitrous oxide pressure in the second chamber, the differential pressure regulator valve is opened so the second chamber is fluidly connected to the second output conduit.

After nitrous oxide has passed through the differential pressure regulator 330, a ratio controlling valve 340 located along the second output conduit 326 allows a user to adjust the flow of the nitrous oxide through the second output conduit.

Beyond this valve 340, the second output conduit 326 joins the first output conduit 324 at a first end of a combined flow conduit 350, in which the oxygen and nitrous oxide are mixed according to the ratio set by the user.

The combined flow conduit 350 extends to an output port 360 on the fluid control system, which can engage a tube for a cannula or another device.

A display unit on the housing of the flow meter has flow meter bars 370A, 370B that show the flow of the oxygen and the nitrous oxide through the first and second output conduits, respectively. This allows a user to more precisely control the ratio of oxygen and nitrous oxide being provided to a patient.

The fluid control system allows a user to flush the output port 360 with oxygen by way of a flush valve 362. The flush valve is moveable between an open position and a closed position. The flush valve 362 is in the closed position during normal operation, such as when the flow meter is being used to mix oxygen and nitrous oxide. When it is desirable to flush the output port with oxygen, the user moves the flush valve to the open position, thereby providing a direct connection between the first intake conduit and the combined output conduit, allowing the oxygen to bypass the first output conduit and differential pressure regulator 330.

Figure 31:
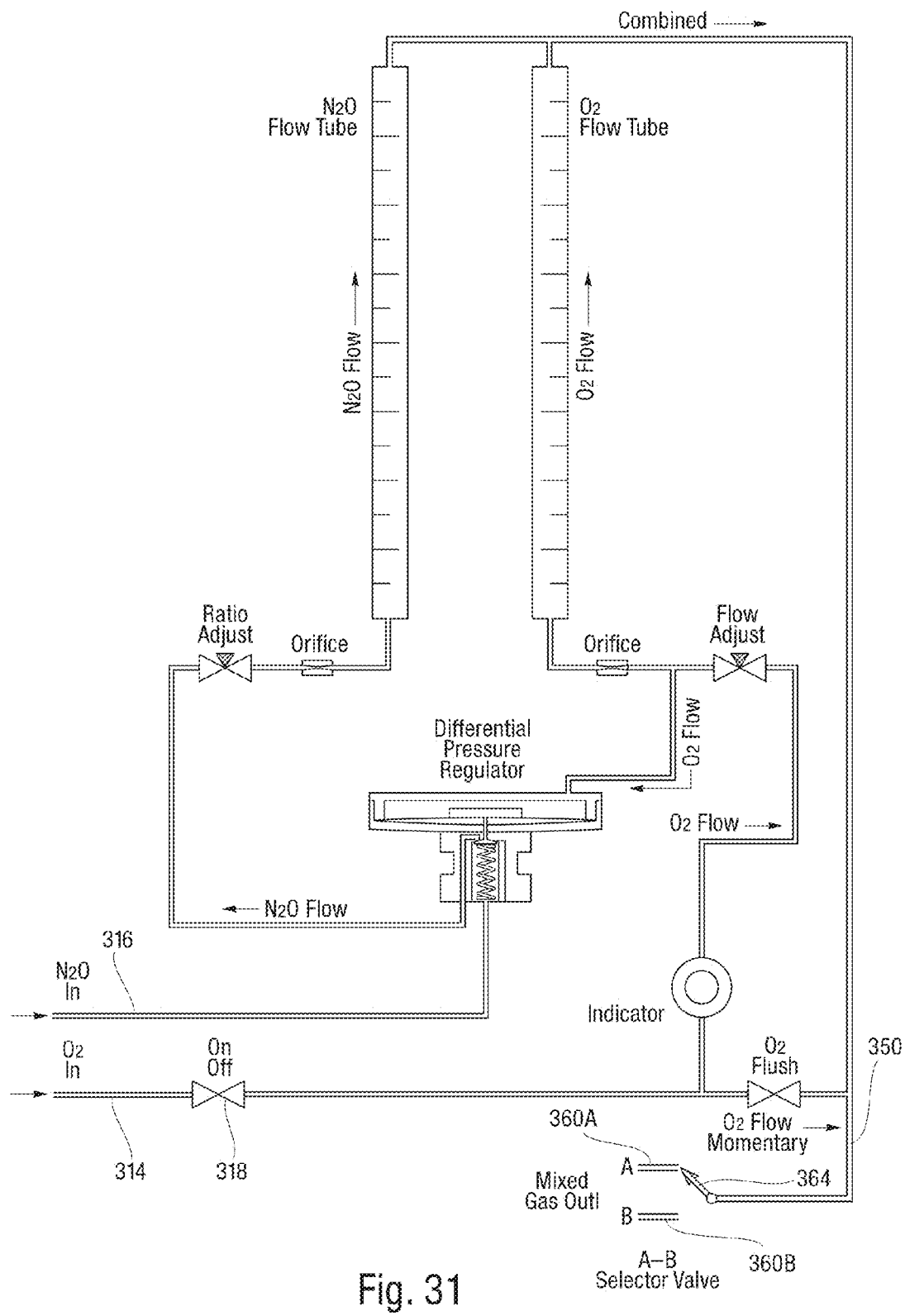
FIG. 31 is a schematic of the fluid control system with an A-B outlet switch.

The embodiment of FIG. 31 includes an A-B selector valve 364, which allows the user to selectively connect the combined output conduit with a first (A) port 360A and a second (B) port 360B on the fluid control system housing 310. While this embodiment has two output ports, additional ports may be provided.

Figure 32:
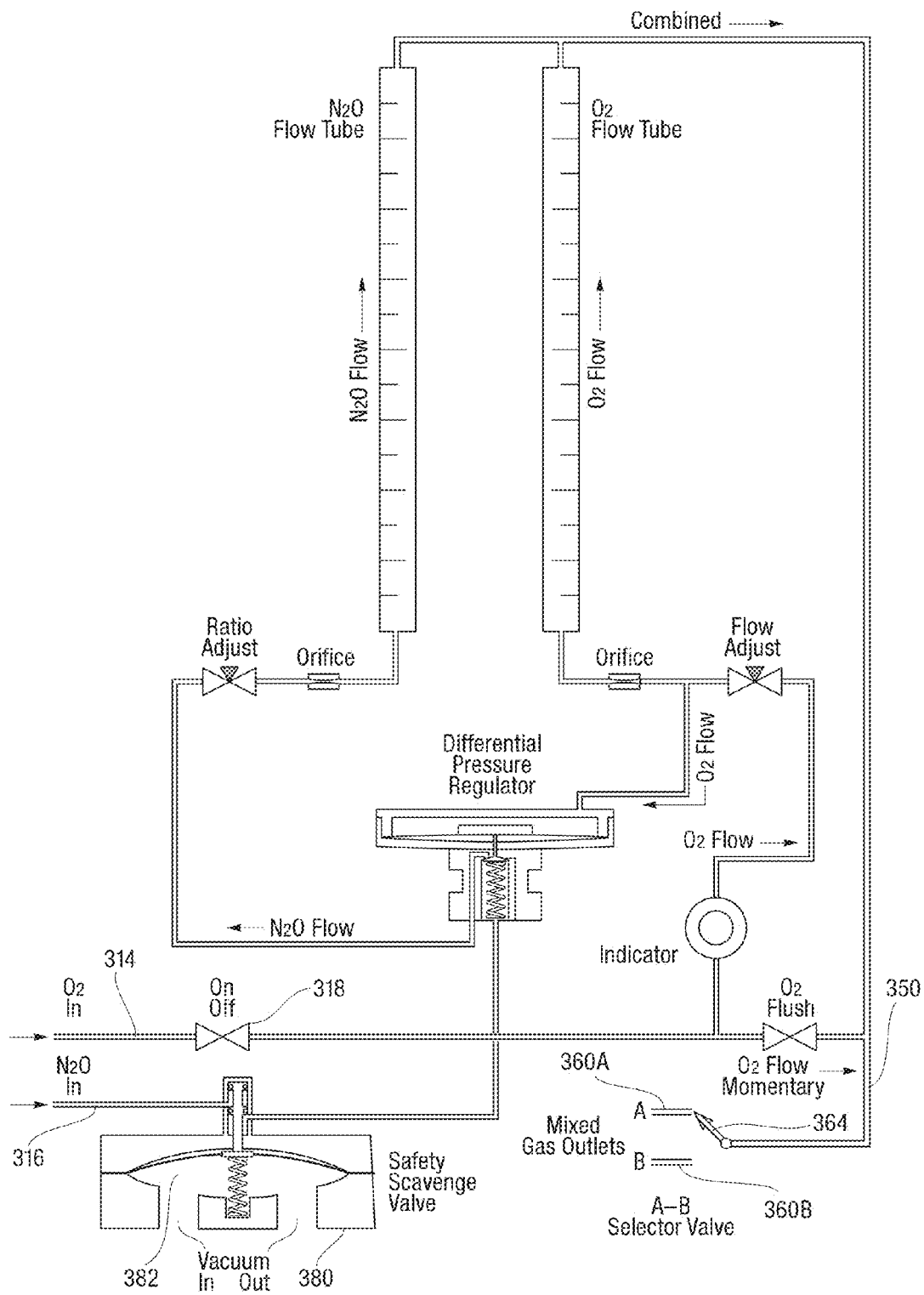
FIG. 32 is a schematic of the fluid control system with a safety scavenge and an A-B outlet switch.

The embodiment of FIG. 32 further includes a safety scavenge valve 380 on the second input conduit. The safety scavenge valve has a spring that causes it to be spring biased to a closed position. A valve chamber 382 is fluidly connected to the scavenge system. When there is sufficient vacuum pressure in the scavenge system, the vacuum pressure in the valve chamber overcomes the spring bias to open the safety scavenge valve, thereby allowing nitrous oxide to flow through the second intake conduit 316.

While the above description relates to mixing oxygen and nitrous oxide, it is possible to use the flow meter to combine other gases or other fluids.

Therefore, while there is shown and described herein certain specific structure embodying the invention, it will be manifest to those skilled in the art that various modifications and rearrangements of the parts may be made without departing from the spirit and scope of the underlying inventive concept and that the same is not limited to the particular forms herein shown and described except insofar as indicated by the scope of the appended claims.

What is claimed is:

1. A system for administering nitrous oxide and oxygen, comprising:
   a fluid control system for controlling a flow of nitrous oxide and oxygen;
   a nitrous oxide and oxygen supply fluidly connected to the fluid control system;
   a vacuum source fluidly connected to the fluid control system;
   a safety scavenge system connected to the fluid control system, the safety scavenge system comprising:
   a mass airflow sensor for reading scavenging vacuum pressure fluidly connected to the vacuum source;
   a master controller in electrical communication with the mass airflow sensor for receiving the scavenging vacuum pressure reading from the mass airflow sensor which is compared to one or more predetermined ranges; and
   a nitrous oxide valve fluidly connected to the nitrous oxide supply and in electrical communication with the master controller which shuts off the nitrous oxide valve when the scavenging vacuum pressure is less than the one or more predetermined ranges;
wherein the fluid control system further comprises:
a first intake conduit and a second intake conduit;
a shutoff valve on the first intake conduit, selectively moveable between an off position in which it does not permit a fluid to flow past a shutoff point in the first intake conduit and an on position in which it does permit a fluid to flow past a shutoff point in the first intake conduit;
a flow controlling valve at a joint between the first intake conduit and a first output conduit, the flow controlling valve allowing the first intake conduit and the first output conduit to be in selective fluid connection;
a differential pressure regulator having a first chamber and a second chamber, the first chamber being fluidly connected with the first output conduit, and the second chamber being fluidly connected with the second intake conduit;
the second chamber of the differential pressure regulator being selectively fluidly connectable with a second output conduit;
the first and second chamber being separated by a wall, the wall being spring biased to a first position in which the second intake conduit is not fluidly connected with the second output conduit, and the wall being displaceable to an open position in which the second intake conduit is fluidly connected with the second output conduit;
a ratio controlling valve on the second output conduit;
a combined flow conduit having a first end that is fluidly connected with the first output conduit and the second output conduit; and
a display unit showing a first flow through the first output conduit, the display unit displaying a second flow through the second output conduit.

2. The system of claim 1, further comprising a flush valve, the flush valve allowing the first intake conduit to be selectively in direct fluid connection with the combined flow conduit.

3. The system of claim 1, further comprising a flow indicator light that indicates whether a fluid is flowing through the first intake conduit.

4. The system of claim 1, further comprising a selector valve allowing the combined output conduit to be in selective fluid engagement with one of a plurality of output ports.

5. The system of claim 1, further comprising a safety scavenge valve on the second input conduit.

6. A method for administering nitrous oxide, comprising the following steps:
providing a fluid flow generated by a vacuum source;
providing nitrous oxide fluid from a nitrous oxide source;
providing oxygen from an oxygen source;
controlling the flow of oxygen through a fluid control system, the fluid control system having a shutoff valve for selectively activating the fluid control system; adjusting a flow controlling valve to modify the oxygen flow through the fluid control system; causing the oxygen pressure within the fluid control system to engage a differential pressure regulator that controls the flow of nitrous oxide through the fluid control system; adjusting the flow of nitrous oxide within the system after the flow of nitrous oxide has passed through the differential pressure regulator;
displaying a relative flow of the oxygen and nitrous oxide in the fluid control system;
combining the nitrous oxide and oxygen before they exit the fluid control system;
connecting a safety scavenge system to a fluid connection between the nitrous oxide source and said vacuum source, the safety scavenge system including:
a mass airflow sensor for reading scavenging vacuum pressure;
a master controller in electrical communication with the mass airflow sensor for receiving a scavenging vacuum pressure reading from the mass airflow sensor which is compared to one or more predetermined ranges; and
a nitrous oxide valve fluidly connected to the nitrous oxide source and in electrical communication with the master controller;
increasing flow rate of the vacuum source to provide fluid into the safety scavenge system;
releasing nitrous oxide through said safety scavenge system upon the vacuum source reaching or exceeding the one or more predetermined ranges; and
shutting off the nitrous oxide valve when the scavenging vacuum pressure is less than the one or more predetermined ranges.

7. A system for administering nitrous oxide and oxygen, comprising:
a fluid control system for controlling a flow of nitrous oxide and oxygen;
a vacuum source fluidly connected to the fluid control system;
a safety scavenge system connected to the fluid control system, the safety scavenge system comprising:
a mass airflow sensor for reading scavenging vacuum pressure fluidly connected to the vacuum source;
a master controller in communication with the mass airflow sensor for receiving the scavenging vacuum pressure and comparing the scavenging vacuum pressure to one or more predetermined ranges; and
a nitrous oxide valve for fluidly connecting to a nitrous oxide supply and in communication with the master controller, which selectively shuts off the nitrous oxide valve when the scavenging vacuum pressure is outside the one or more predetermined ranges.

8. The system of claim 7, further comprising a nitrous oxide and oxygen supply fluidly connected to the fluid control system.

9. The system of claim 7, wherein the fluid control system further comprises:
a first intake conduit and a second intake conduit;
a shutoff valve on the first intake conduit, selectively moveable between an off position in which the shut-off valve does not permit a fluid to flow past a shutoff point in the first intake conduit and an on position in which the shutoff valve does permit a fluid to flow past a shutoff point in the first intake conduit.

10. The system of claim 8, further comprising:
a flow controlling valve at a joint between the first intake conduit and a first output conduit, the flow controlling valve allowing the first intake conduit and first output conduit to be in selective fluid connection;
a differential pressure regulator having a first chamber and a second chamber, the first chamber being fluidly connected with the first output conduit, and the second chamber being fluidly connected with the second intake conduit;
the second chamber of the differential pressure regulator being selectively fluidly connectable with a second output conduit; and the first and second chamber being separated by a wall, the wall being spring biased to a first position in which the second intake conduit is not fluidly connected with the second output conduit, and the wall being displaceable to an open position in which the second intake conduit is fluidly connected with the second output conduit.

11. The system of claim 10, further comprising a ratio controlling valve on the second output conduit.

12. The system of claim 10, further comprising a combined flow conduit having a first end that is fluidly connected with the first output conduit and the second output conduit; and a display unit showing a first flow through the first output conduit.

13. The system of claim 12, wherein the display unit displays a second flow through the second output conduit.

14. The system of claim 10, further comprising a flush valve, the flush valve allowing the first intake conduit to be selectively in direct fluid connection with the combined flow conduit.

15. The system of claim 10, further comprising a flow indicator light that indicates whether a fluid is flowing through the first intake conduit.

16. The system of claim 10, further comprising a selector valve allowing the combined output conduit to be in selective fluid engagement with one of a plurality of output ports.

* * * * *